(12) United States Patent
Cotrufo et al.

(10) Patent No.: US 12,326,460 B2
(45) Date of Patent: Jun. 10, 2025

(54) SOIL ORGANIC MATTER DENSITY FRACTIONATION DEVICES AND METHODS

(71) Applicant: COLORADO STATE UNIVERSITY RESEARCH FOUNDATION, Fort Collins, CO (US)

(72) Inventors: Maria Francesca Cotrufo, Fort Collins, CO (US); Michelle Haddix, Fort Collins, CO (US); Rebecca Even, Fort Collins, CO (US); Kolbin Dahley, Denver, CO (US); Travis Johnson, Fort Collins, CO (US); Andrew Kollar, Fort Collins, CO (US); Jayvin Krzych, Fort Collins, CO (US); Kyle Palmiscno, Loveland, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 350 days.

(21) Appl. No.: 18/094,254

(22) Filed: Jan. 6, 2023

(65) Prior Publication Data
US 2023/0213545 A1    Jul. 6, 2023

Related U.S. Application Data

(60) Provisional application No. 63/296,988, filed on Jan. 6, 2022.

(51) Int. Cl.
*G01N 35/10* (2006.01)
*G01N 35/00* (2006.01)

(52) U.S. Cl.
CPC ..... *G01N 35/1083* (2013.01); *G01N 35/1004* (2013.01); *G01N 2035/00485* (2013.01); *G01N 2035/1088* (2013.01)

(58) Field of Classification Search
CPC ............ C12Q 1/6886; C12Q 2600/154; G01N 1/4077; G01N 2001/4088; G01N 2035/00485; G01N 2035/1088; G01N 33/24; G01N 35/025; G01N 35/1004; G01N 35/1011; G01N 35/1083
See application file for complete search history.

(56) References Cited

U.S. PATENT DOCUMENTS

| | | | |
|---|---|---|---|
| 2020/0400518 A1* | 12/2020 | McKay | G01S 17/894 |
| 2023/0213545 A1* | 7/2023 | Cotrufo | G01N 33/24 |
| | | | 73/863.24 |

\* cited by examiner

*Primary Examiner* — Kristina M Deherrera
*Assistant Examiner* — Gedeon M Kidanu
(74) *Attorney, Agent, or Firm* — Quarles & Brady LLP

(57) ABSTRACT

A soil fractionation system can include a plurality of sample racks propelled by a drive system. Each sample rack can include a sample tube for holding a soil sample and a filter cup for receiving an extracted fraction of the soil sample. An extractor module of the fractionation system can include an extractor assembly and a filter assembly. A control system can control the relative positioning of the plurality of sample racks via the drive system, the relative movement between the extractor assembly and the sample tube, and the relative movement between the filter assembly and the filter cup.

20 Claims, 29 Drawing Sheets

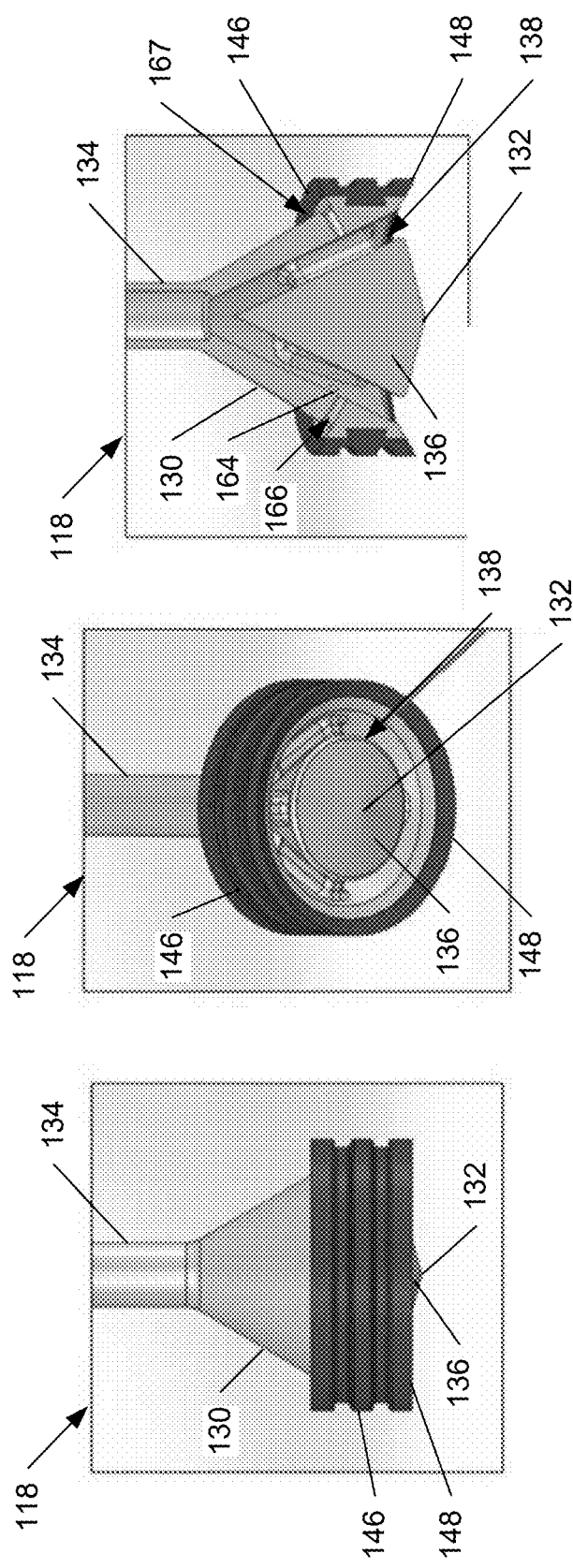

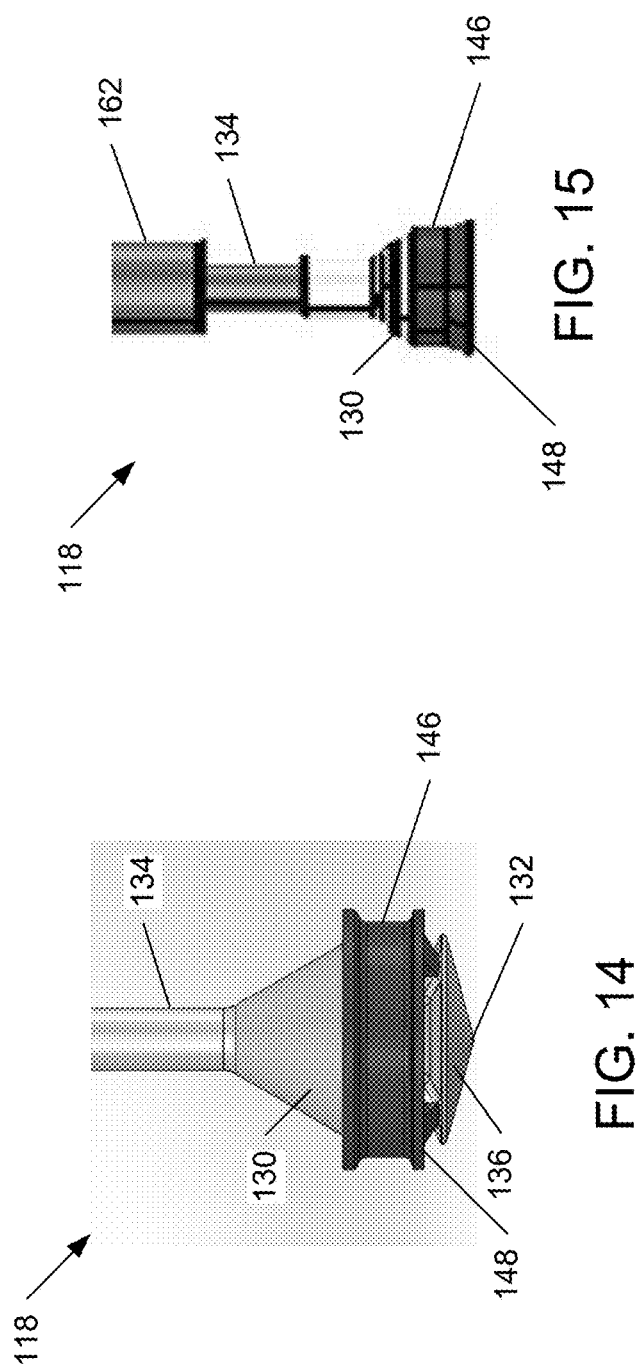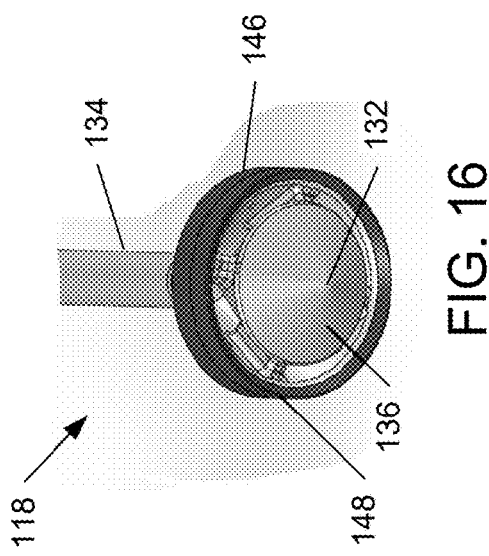

SOIL ORGANIC MATTER DENSITY FRACTIONATION DEVICES AND METHODS

CROSS-REFERENCE TO RELATED APPLICATION

This application claims priority to U.S. Provisional Patent Application No. 63/296,988, filed Jan. 6, 2022, which is incorporated by reference herein in its entirety.

STATEMENT CONCERNING FEDERALLY SPONSORED RESEARCH AND DEVELOPMENT

This invention was made with government support under grant 2044760 awarded by the National Science Foundation. The government has certain rights in the invention.

TECHNICAL FIELD

The present disclosure is generally related to soil organic matter fractionation. More particularly, the disclosure encompasses soil organic matter density fractionation devices and methods.

BACKGROUND

Soils have the capacity to store vast amounts of soil organic matter (SOM), which aids in provision of multiple ecosystem services and is widely recognized as a viable component of a diversified strategy to address sustainability goals. Managing SOM stocks to effectively analyze soil components and address global challenges requires deep understanding of SOM formation, persistence, and function, which is aided by separating SOM into a light and a dense fraction.

SUMMARY

Some embodiments described herein provide a fractionation system having an extractor module and a plurality of sample racks.

Embodiments of the invention provide a soil fractionation system for separating fractions of soil of different densities. The soil fractionation system can include a plurality of sample racks, an extractor module, and control system. The plurality of sample racks can be propelled by a drive system. Each sample rack can include a sample tube for holding a soil sample and a filter cup. The sample tube can define a sample tube opening and the filter cup can define a filter cup opening at a top of the filter cup. The filter cup can be configured to receive an extracted fraction of the soil sample and can include a filter. The filter can be disposed at a bottom of the filter cup. The extraction module can include an extractor assembly and a filter assembly. The extractor assembly can include an extractor nozzle dimensioned to be inserted into the sample tube. The filter assembly can include a first filter sealing member that is dimensioned to sealingly engage the filter cup opening at the top of the filter cup and a second filter sealing member dimensioned to sealingly engage the filter cup at the bottom of the filter cup adjacent to the filter. The control system can control the relative positioning of the plurality of sample racks via the drive system, the relative movement between the extractor assembly and the sample tube, and the relative movement between the filter assembly and the filter cup.

Some embodiments of the invention provide an extractor module for a fractionation system. The extractor module can include an extractor assembly, a filter assembly, a first linear actuator, and a second linear actuator. The extractor module can include an extractor nozzle that is disposed at a distal end of a conduit. The extractor nozzle can be configured to be inserted into a soil sample having a light soil fraction suspended above a heavy soil fraction. The filter assembly can include first and second sealing members. The first sealing member can be fluidly coupled to a first tube and the second sealing member can be fluidly coupled to a vacuum chamber. The first linear actuator can be configured for relative movement of the extractor assembly and the second linear actuator can be configured for relative movement of the filter assembly.

Some embodiments of the invention provide a method of separating soil fractions. The method can include moving a first sample rack having a sample tube and a filter cup into an extractor module. An extractor nozzle can be inserted into the sample tube. The sample tube can have a first soil fraction suspended above a second soil fraction. The first sealing member can be moved into engagement with a top of a filter cup. A second sealing member can be moved into engagement with a bottom of the filter cup. A vacuum can be formed within the filter cup. The first soil fraction can be transferred via the vacuum from the sample tube to the filter cup through a conduit that fluidly couples the extractor nozzle to the first sealing member. The extractor nozzle can be removed from the sample tube and the first and second sealing members can be disengaged from the filter cup. A second sample rack can then be moved into the extraction module as the first sample rack is moved away from the extraction module

BRIEF DESCRIPTION OF THE DRAWINGS

The following detailed description is to be read with reference to the figures, in which like elements in different figures have like reference numerals. The figures, which are not necessarily to scale, depict selected embodiments and are not intended to limit the scope of embodiments of the invention. Given the benefit of this disclosure, skilled artisans will recognize the examples provided herein have many useful alternatives that fall within the scope of the invention.

FIG. 11 is a side view of an extractor nozzle according to another embodiment of the invention.

FIG. 12 is a bottom isometric view of the extractor nozzle of FIG. 11.

FIG. 13 is a side cross-sectional view of the extractor nozzle of FIG. 11.

FIG. 14 is a side view of an extractor nozzle according to another embodiment of the invention.

FIG. 15 is a side view of an extractor nozzle according to another embodiment of the invention.

FIG. 16 a bottom isometric view of an extractor nozzle according to another embodiment of the invention.

DETAILED DESCRIPTION

Figure 1:
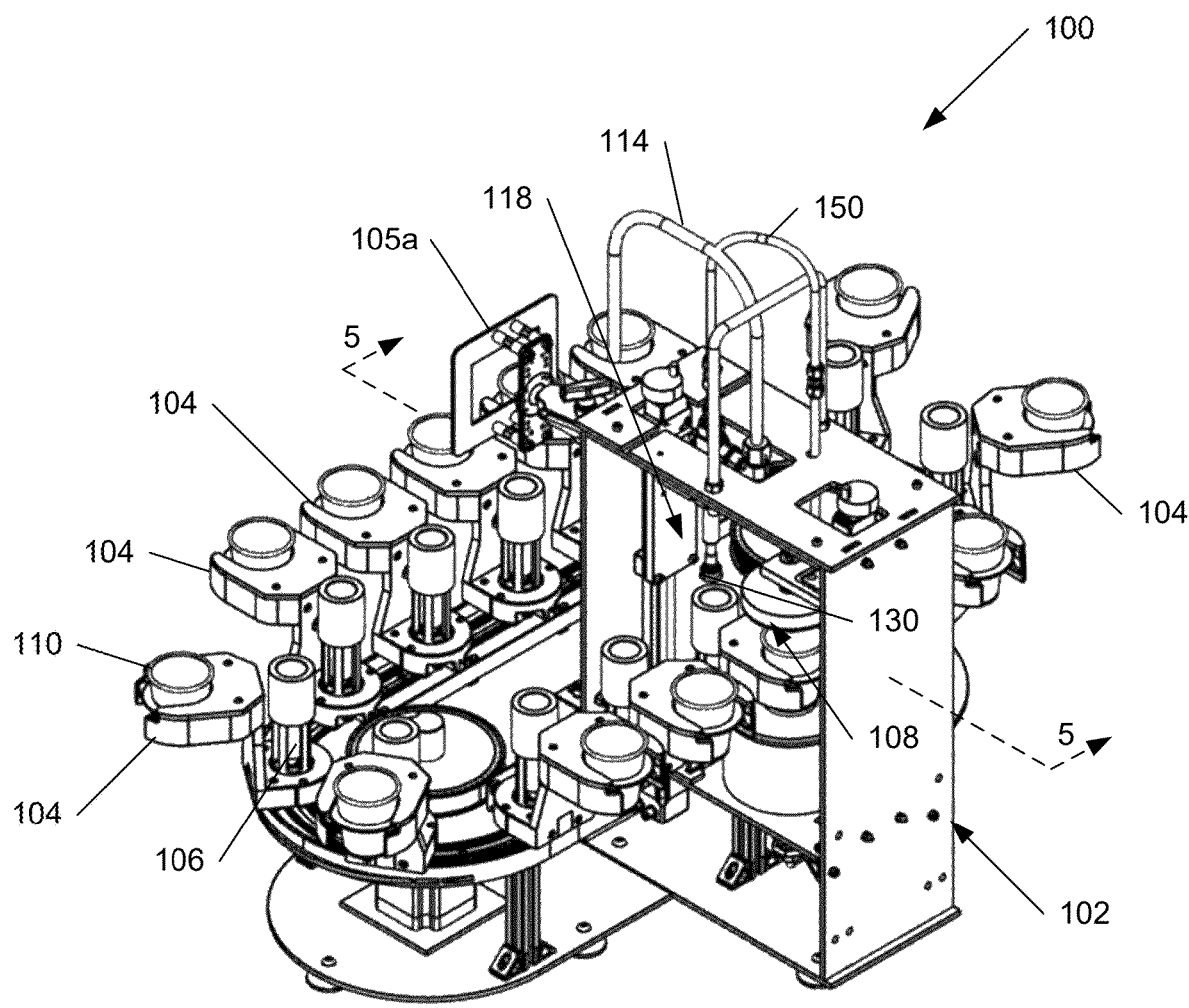
FIG. 1 is an isometric view of a fractionation system according to an embodiment of the invention.

The following discussion is presented to enable a person skilled in the art to make and use examples of the disclosed technology. Various modifications to the illustrated examples will be readily apparent to those skilled in the art, and the generic principles herein can be applied to other examples and applications without departing from the disclosed technology. Thus, examples of the disclosed technology are not intended to be limited to examples shown, but are to be accorded the widest scope consistent with the principles and features disclosed herein. The following detailed description is to be read with reference to the figures, in which like elements in different figures have like reference numerals. The figures, which are not necessarily to scale, depict selected examples and are not intended to limit the scope of examples of the disclosed technology. Skilled artisans will recognize the examples provided herein have many useful alternatives and fall within the scope of disclosed technology.

Before any examples of the disclosed technology are explained in detail, it is to be understood that the disclosed technology is not limited in its application to the details of construction and the arrangement of components set forth in the following description or illustrated in the attached drawings. The disclosed technology is capable of other examples and of being practiced or of being carried out in various ways. Also, it is to be understood that the phraseology and terminology used herein is for the purpose of description and should not be regarded as limiting. For example, the use of "including," "comprising," or "having" and variations thereof herein is meant to encompass the items listed thereafter and equivalents thereof as well as additional items.

As used herein, unless otherwise specified or limited, the terms "mounted," "connected," "supported," "secured," and "coupled" and variations thereof, as used with reference to physical connections, are used broadly and encompass both direct and indirect mountings, connections, supports, and couplings. Further, unless otherwise specified or limited, "connected," "attached," or "coupled" are not restricted to physical or mechanical connections, attachments, or couplings.

Also as used herein, unless otherwise limited or defined, "or" indicates a non-exclusive list of components or operations that can be present in any variety of combinations, rather than an exclusive list of components that can be present only as alternatives to each other. For example, a list of "A, B, or C" indicates options of: A; B; C; A and B; A and C; B and C; and A, B, and C. Correspondingly, the term "or" as used herein is intended to indicate exclusive alternatives only when preceded by terms of exclusivity, such as "only one of," or "exactly one of." For example, a list of "only one of A, B, or C" indicates options of: A, but not B and C; B, but not A and C; and C, but not A and B. In contrast, a list preceded by "one or more" (and variations thereon) and including "or" to separate listed elements indicates options of one or more of any or all of the listed elements. For example, the phrases "one or more of A, B, or C" and "at least one of A, B, or C" indicate options of: one or more A; one or more B; one or more C; one or more A and one or more B; one or more B and one or more C; one or more A and one or more C; and one or more A, one or more B, and one or more C. Similarly, a list preceded by "a plurality of" (and variations thereon) and including "or" to separate listed elements indicates options of multiple instances of any or all of the listed elements. For example, the phrases "a plurality of A, B, or C" and "two or more of A, B, or C" indicate options of: one or more A and one or more B; one or more B and one or more C; one or more A and one or more C; and one or more A, one or more B, and one or more C.

In some implementations, devices or systems disclosed herein can be utilized, manufactured, installed, etc. using methods embodying aspects of the invention. Correspondingly, any description herein of particular features, capabilities, or intended purposes of a device or system is generally intended to include disclosure of a method of using such devices for the intended purposes, of a method of otherwise implementing such capabilities, of a method of manufacturing relevant components of such a device or system (or the device or system as a whole), and of a method of installing disclosed (or otherwise known) components to support such purposes or capabilities. Similarly, unless otherwise indicated or limited, discussion herein of any method of manufacturing or using for a particular device or system, including installing the device or system, is intended to inherently include disclosure, as embodiments of the invention, of the utilized features and implemented capabilities of such device or system.

In general, soil organic matter (SOM) can refer to the fraction of soil that consists of organic compounds of plant, microbial, or animal origins in various stages of decomposition. Fractions within soil organic matter can include free light fractions (e.g., having a density of less than approximately 1.6 to 1.85 $g/cm^3$) and fractions associated with minerals and are therefore heavy (having a density that is greater than approximately 1.6 to 1.85 $g/cm^3$). Having relatively high levels of organic matter stabilized by mineral association (i.e. heavy fractions) in soil can sequester carbon away from the atmosphere. Light organic matter can help build soil structure by stimulating aggregation, and thus promote water infiltration and holding. Further the turnover of organic matter recycles nutrients. Thus, the world's soils can be considered an important battleground in the fight climate change, food production, and other global challenges.

Soils have the capacity to store vast amounts of soil organic matter, which can aid in the provision of multiple ecosystem services. Managing soil organic matter stocks to effectively address global challenges requires a deep understanding of soil organic matter formation, persistence, and function. In this regard, it can be useful to categorize and separate soil organic matter into different fractions, such as a light fraction and a dense fraction.

Conventional methods for separating soil organic matter into light and dense fractions (i.e., physical fractionation) often requires a labor-intensive manual process that requires highly trained personnel. Even with the use of skilled personnel, conventional procedures typically have very low throughout with an estimated rate of 20 samples per week. Because of the low throughput and high labor costs associated with conventional methods, analytical test facilities often are reluctant to offer soil organic matter physical fractionation.

Embodiments of the present disclosure address these and other drawbacks of conventional fractionation. For example, embodiments of the present disclosure provide systems and methods of soil organic matter physical fractionation on a plurality of soil samples sequentially without having to stop between samples. Embodiments of the present disclosure can provide a system that not only automates aspects, but appreciably improves fractionation and fractionation quality. Further, the fractionation system according to embodiments of the present disclosure can lower the cost and operator skill set required operate one or more fractionation operations, increase throughput, and provide methods for scaling fractionation operations.

Current fractionation methods can include a plurality of steps. In conventional methods, before physical separation can be performed, a variety of steps must be taken to separate different density materials within a sample tube. Density separation can require the use of a known density fluid and a centrifuge. A fluid and prepared soil sample can be combined in a closed tube mixed and centrifuged to allow the light and heavy fraction to separate. After being removed from the centrifuge, the sample can be separated, with the light fraction generally floating on top of the fluid and the heavy fraction can be generally compacted at the bottom of the sample. Next, in conventional methods, trained laboratory personnel can remove the light fraction and remaining fluid using a suction tube and a filter-type assembly.

To remove the light fraction soil organic matter from a sample tube, trained personnel can precisely insert a nozzle into the sample tube at the fluid plane to suck up the light fraction. As the fluid level in the tube drops, residual light fraction material can remain on the wall of the tube. This material then needs to be scraped off the sides of the tube using a precise tool. Fluid removal can continue until all of the light fraction and residual fluid is removed. As the fluid level reaches the bottom and approaches the heavy fraction of material, precise care must be taken to ensure that none of the heavy fraction material is agitated or removed through the extraction process. In general, this process is time consuming, requires a high degree of accuracy and precision, and can only be applied to a single sample before a reset process rinses the extractor to accommodate use with a subsequent sample.

Embodiments of the invention can provide a soil organic matter physical fractionation device that can separate soil fractions automatically, precisely, and accurately with a high degree of repeatability. In particular, the system according to embodiments of the invention can process a high capacity of samples continuously without, or with minimal, user interaction. In some embodiments, the entire system can be enclosed to prevent debris from getting into sample containers. The device can include a plurality or chain of sample holders that may be fed through a soil organic matter light fraction extractor station. Each sample holder can include a filter that allows the samples to be stored separately and can eliminate a requirement for user interaction between extractions. In some embodiments, the system can include a control interface and one or more sensors to progress a sample chain from one sample to the next and locate each sample accurately within an extractor station. A user interface can allow for laboratory (or other) personnel to adjust certain parameters of operation prior to a cycle, such as number of samples, volume of rinse water, and others.

Figure 2:
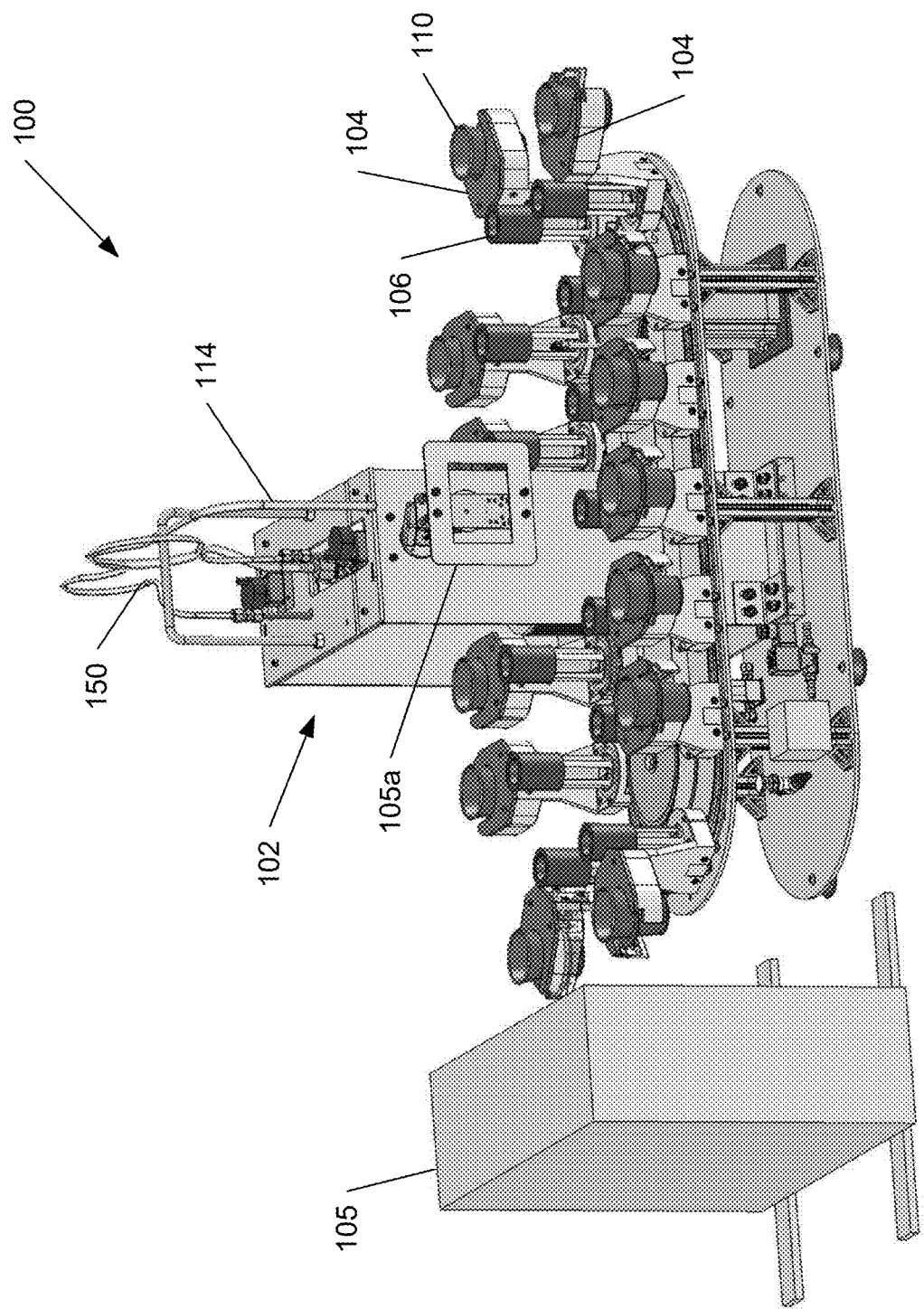
FIG. 2 is another isomeric view of the fractionation system of FIG. 1.

With reference to FIGS. 1 and 2, a fractionation system 100 can include an extractor module 102 and a plurality of sample racks 104. In general, the extractor module 102 is responsible for removing soil organic matter light fraction and residual fluid from a sample tube 106 or other sample holder. A filter assembly 108 can be used to capture the soil organic matter that is extracted from the sample tube 106 via an extractor assembly 118. A filter cup 110 can travel with each sample tube 106 on a sample rack 104. A filter sealing assembly 108 can seal a top of a filter cup 110 to create a seal with the cup 110 to allow the filter cup 110 to be used as a vacuum chamber. As shown in FIG. 2, the fractionation system 100 can further include a control system 105, as will be described in greater detail below. In some embodiments, the control system 105 can include a mount 105a for a user interface device, as shown in FIGS. 1 and 2.

Figure 3:
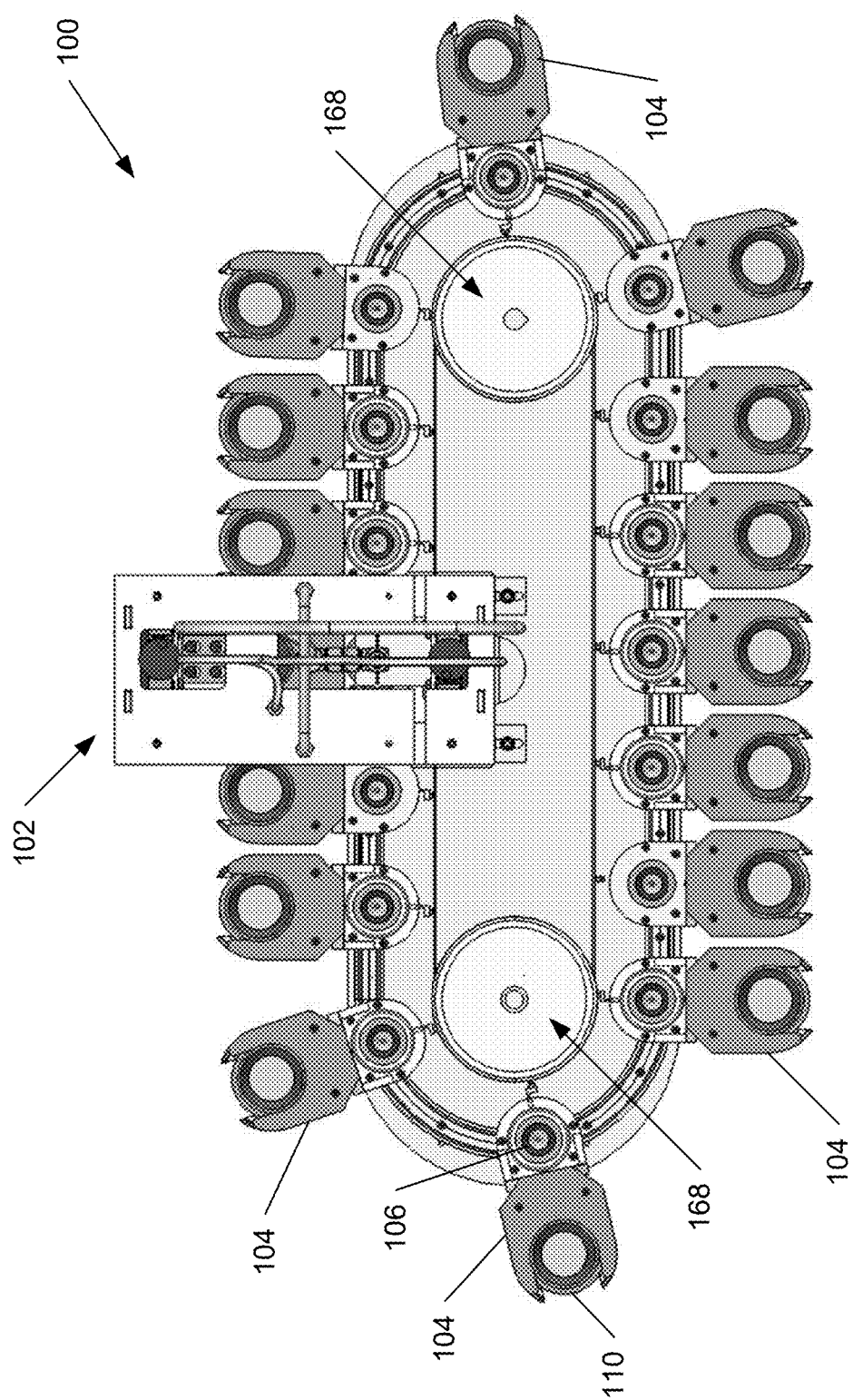
FIG. 3 is a top view of the fractionation system of FIG. 1.
Figure 26:
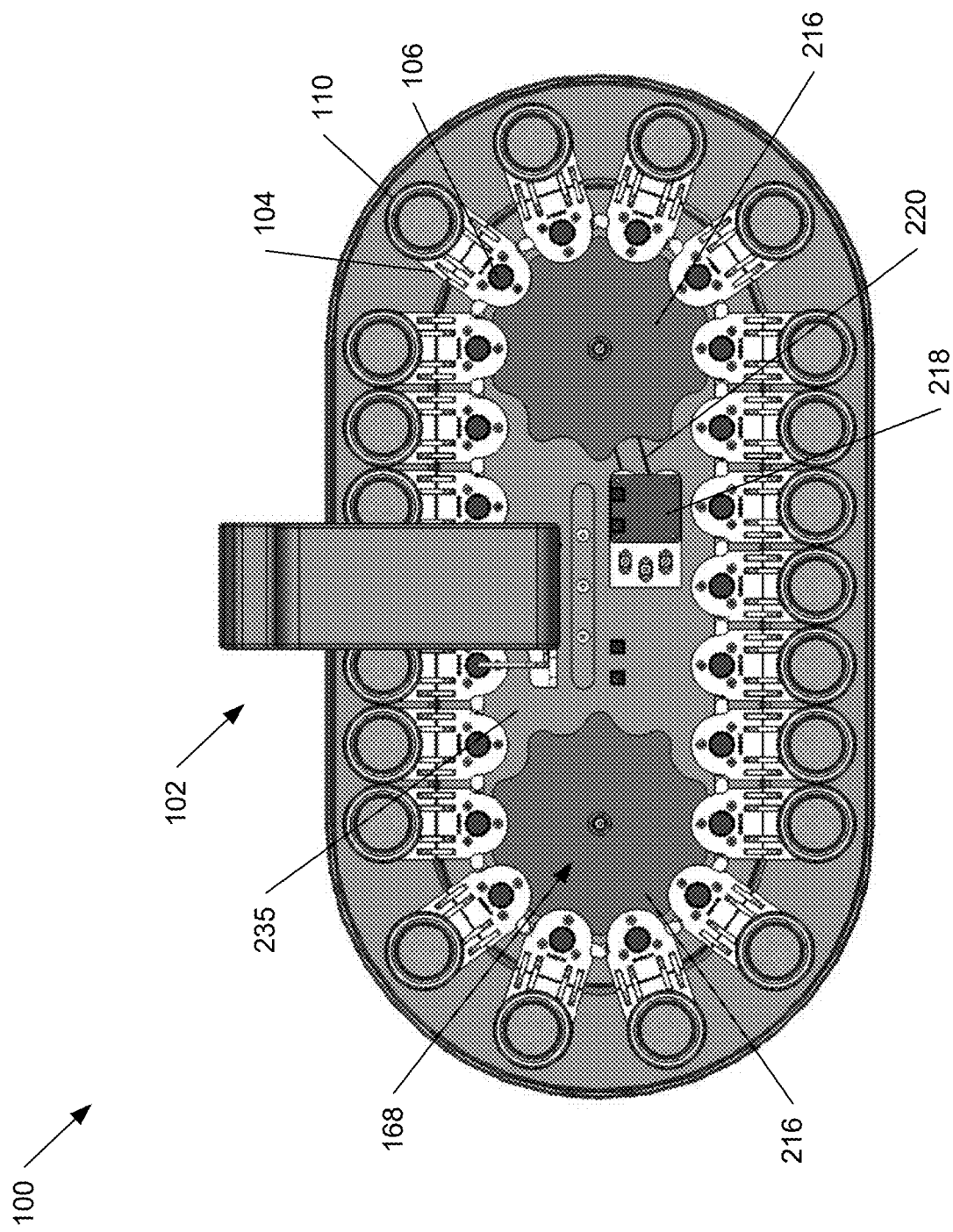
FIG. 26 is a top view of the fractionation system of FIG. 25.

FIG. 3 illustrates a top view of the fractionation system 100 and a drive system 168. The drive system 168 in the illustrated embodiment can include a driven gear and an idler gear that drive a belt to which each sample rack 104 is relatively secured to. However, in other embodiments, other drive systems 168 are possible (see, for example, FIGS. 26, 33, and 34).

Figure 4:
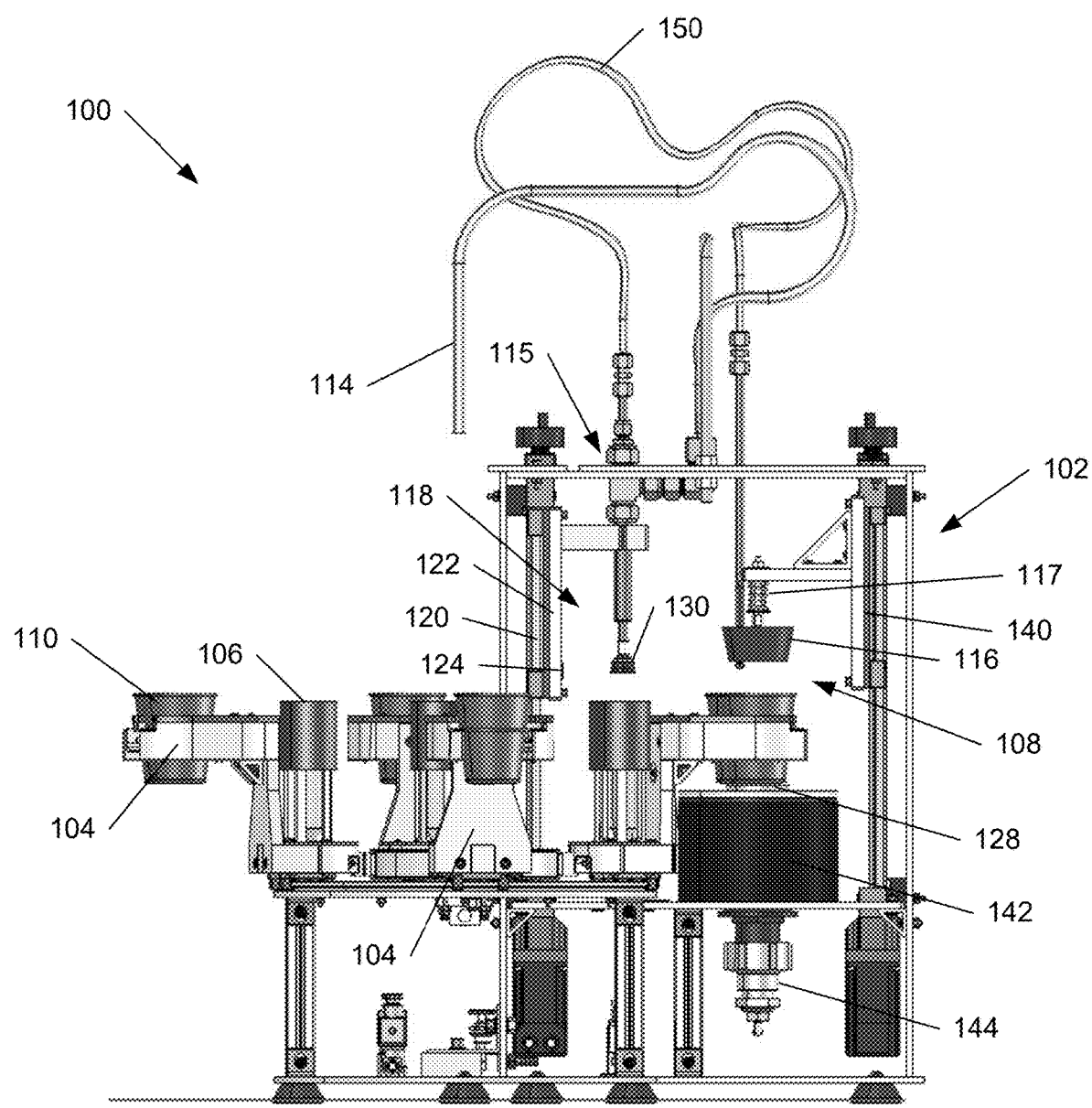
FIG. 4 is a side view of the fractionation system of FIG. 1.
Figure 5:
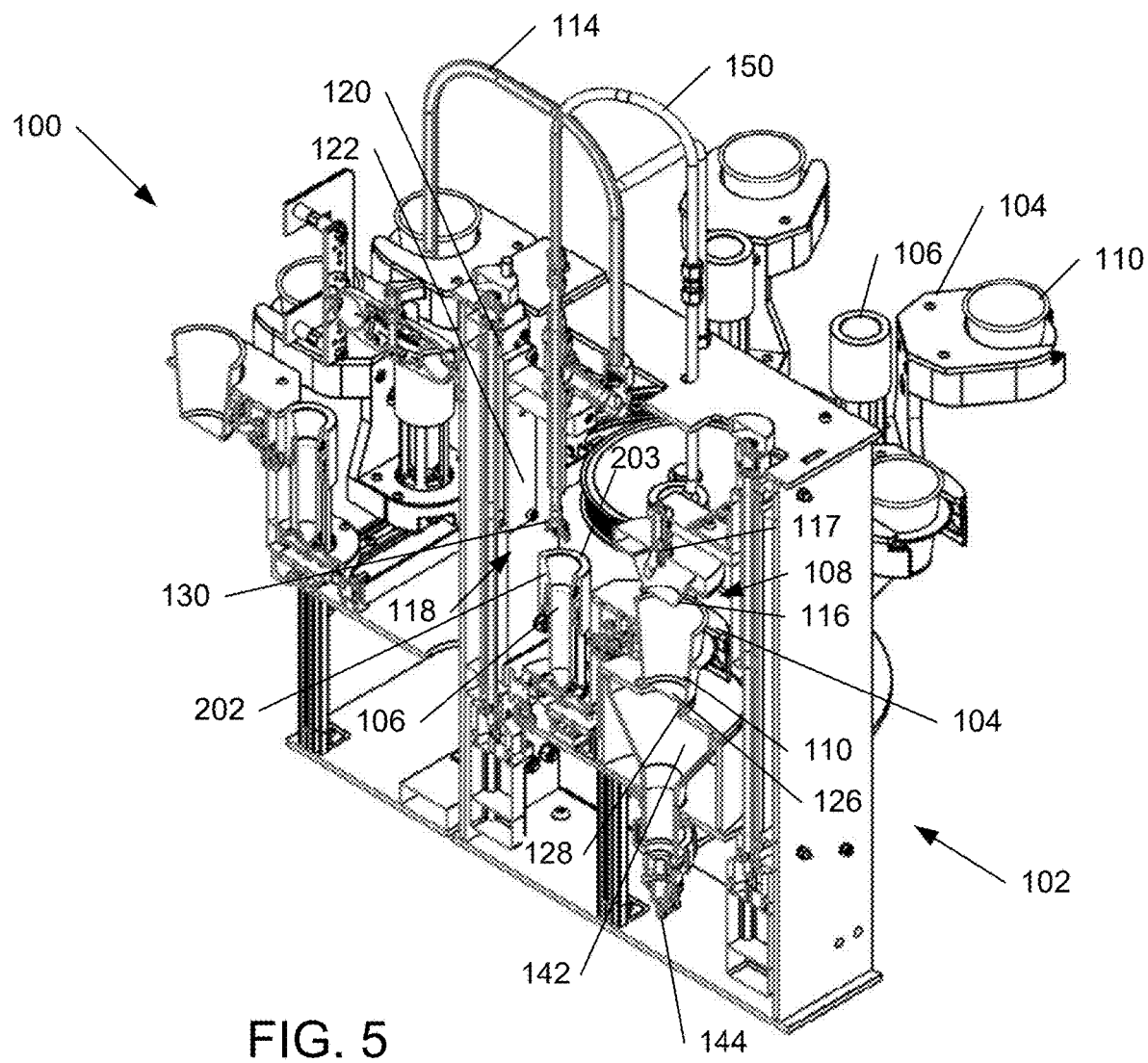
FIG. 5 is an isometric cross-sectional view of the fractionation system taken along line 5-5 of FIG. 1.

As shown in FIGS. 4 and 5, fractionation system 100 is configured to position a sample tube 106 below an extractor nozzle 130. Once aligned, the extractor nozzle 130 can move vertically relative to the sample tube 106 and into and out of the sample tube 106 to perform an extraction. The extractor nozzle 130 can be mounted on a linear actuator 120. The linear actuator 120 can be configured to move the extractor nozzle 130 up and down in a vertical motion. The linear actuator 120 can include a movable carriage 122. The extractor nozzle 130 can be secured to the movable carriage 122. In some embodiments, the linear actuator 120 can include a ball screw and be belt driven via a stepper motor. However, other linear motion devices are possible.

In some embodiments, the linear motion may be controlled via sensor feedback. For example, sensor or encoder feedback may be used to monitor and respond to the position of the linear actuator 120. Encoder feedback can provide information on the position of the carriage 122, and therefore the position of the extractor nozzle 130. The actuator 120 can allow for varying speed of the extractor nozzle 130 in the vertical direction as the extractor nozzle 130 is inserted into or removed from the sample tube 106. This variability in speed and positioning of the movable carriage 122 can also allow the extractor nozzle 130 to stop in particular positions during the extraction process to facilitate precise and complete extraction.

In use, the extractor nozzle 130 can be inserted into a sample tube 106 and a vacuum can be applied to remove the soil organic matter light fraction and residual fluid. The vacuum may be provided by a vacuum source that is integral with the fractionation system 100 or otherwise plumbed into the fractionation system 100. The acceleration and speed that the extractor nozzle 130, and in particular, an insert tip 132 of the extractor nozzle 130, is moved into the sample tube 106 is controlled by the linear actuator 120. The distance the extractor nozzle 130 moves into the sample tube 106 can be dictated by the proximity of the extractor head of the extractor nozzle 130 to the soil organic matter heavy fraction at the bottom of the sample tube 106. The head or insert tip 132 is preferably inserted far enough into the sample tube 106 to remove a majority of the residual fluid but avoids moving down so far as to disturb or remove any of the soil organic matter heavy fraction material.

Figure 32:
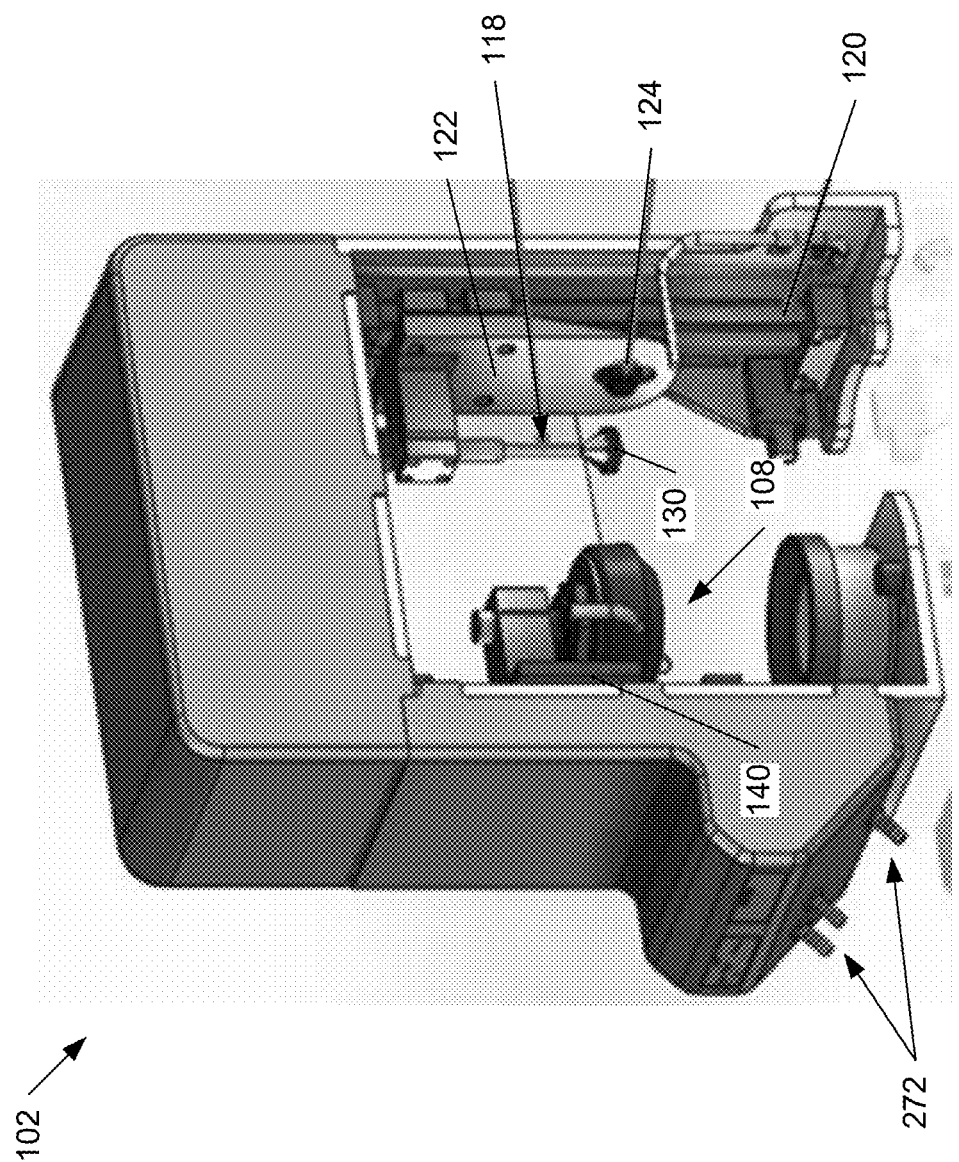
FIG. 32 is an isometric view of an extractor module of the fractionation system of FIG. 30.

In some embodiments, in order to sense the location of the soil organic matter heavy fraction within the particular sample tube 106, the extractor module 102 can include a sensor, such as an optical sensor 124 (see also FIG. 32). For example, the optical sensor 124 can be incorporated into the movable carriage 122 or other sections of the extractor nozzle holder 130. The optical sensor 124 can be positioned below the insert tip 132 of the extractor nozzle 130. In some embodiments, the optical sensor 124 can move with the extractor nozzle 130 via the linear actuator 120 so that the optical sensor 124 remains stationary relative to the extractor nozzle 130. The optical sensor 124 can be configured to detect the relative transparency through a sample tube 106 and detect the presence of the dense heavy fraction collected at the bottom of the sample tube 106. In general, detection of the heavy fraction can provide a control system with an indication that the linear actuator 120 should stop downward motion. Given the benefit of this disclosure, one skilled in the art will appreciate that a variety of available sensors (e.g., distance or proximity sensors, including optical (e.g., camera with image-based control algorithm), ultrasonic, infrared, laser-based (e.g., LiDAR), inductive, capacitive, LED) may be incorporated to detect the transition from light to heavy fraction within the sample tube 106.

For example, the control system 105 can include one or more processors, associated memory storing instructions/algorithms, and communication hardware/protocols (e.g., wired or wireless connections). In addition, the control system 105 can, for instance, receive inputs from one or more sensors (e.g., positional, optical, etc.) or control devices (e.g., stepper motors, actuators, etc.) within the fractionation system 100. In some embodiments, a fraction sensor, such as the optical sensor 124, can send information to the controller related to the position of soil fractions within a sample. In particular, a fraction sensor can signal to the controller when the linear actuator 120 (or other actuators) should move or alter the relative placement of components of the fractionation system 100, including the filter assembly 108 and the extractor assembly 118 of the extractor module 102. Additionally, the control system can receive one or more inputs or signals from a rack sensor or other indexing system related to a position of one or more sample racks 104 along a track or circuit. The control system 105 can then be used to advance, pause, or retract sample racks 104 within the fractionation system. Thus, the control system 105 can control at least the relative position of the plurality of sample racks 104, the relative movement between the extractor assembly 118 and the sample tube 106, and the relative movement between the filter assembly 108 and the filter cup 110.

With continued reference to FIGS. 4 and 5, solids extracted from a sample tube 106 can be collected on a filter 126 of the filter cup 110. The filter 126 can be held within a vacuum chamber 142 and then later rinsed into a drying pan. The fractionation system 100 can employ individual filters 126 for each sample held within a filter cup 110. The filter cup 110 can be clamped between a first filter sealing member 116 configured as a top sealing member and a second sealing member 128 configured as a bottom sealing member 128. The first and second sealing members 116, 128 can create a sealed chamber within the filter cup 110 through which a vacuum can be pulled.

The filter sealing assembly 116 can further include a biasing member, such as a spring 117, in series with the filter sealing member 116. The spring 117 can provide a sealing compressive force when the sealing member 116 is in contact with the filter cup 110 to provide a seal and thereby facilitate the formation of a vacuum within the filter cup 110. While the biasing member is illustrated as a helical spring, given the benefit of this disclosure, one skilled in the art will appreciate that the biasing member may comprise resilient/compressible materials, pneumatic devices, or other structures that help provide a compressive force while also preferably accounting for relative engagement between the sealing surfaces. Each of the sealing members 116, 128 can included tapered end portions adjacent to where each of the respective sealing members 116, 128 engage the filter cup 110. The tapered portions can allow for proper alignment of the sealing members 116, 128 relative to the filter cup 110 so that a reliable vacuum can be formed within the filter cup 110 even if there is a slight axial misalignment of the sealing members 116, 128 relative to the filter cup 110. In this regard, the sealing members 116, 128 can provide self-centering geometries relative to the filter cup 110 which can reduce complex or high-precision tolerance requirements.

In use, fluid can be plumbed from the extractor assembly 118 to the filter assembly 108 via a tube or conduit 150. The tube 150 may be a flexible tube that passes through the top seal 116. A hole in the top of the seal 116 can direct an injector tube into the filler cup 110 so that fluid is injected substantially tangentially into the filter cup 110. The tangential injection can prevent fluid from splashing as it is injected. Eliminating splash can advantageously reduce or eliminate the need to clean the top seal 116 as no or minimal residual will be left behind on the top seal 116.

When fluid is extracted from the sample tube 106 it can pass through the filter cup 110 and into the container or vacuum chamber 142 with the attached bottom filter seal 128. A tube 144 can be connected to this container 142 via a barbed fitting. The opposite end of the tube 144 can be connected to a set of valves (e.g., solenoid valves). These valves can direct the fluid to either a recycle or waste vacuum flask (not shown).

Generally, the known density fluid used to separate the SOM light and heavy fraction is a water-based solution. According to some embodiments of the invention, a solution of sodium polytungstate can be mixed with water to create the known density fluid. This fluid can be recycled and reused for later separations. In some embodiments, the fluid, as well as deionized water use for rinsing, can be collected in the same vacuum flask. Conventionally, the dilution significantly changes the density of the fluid, typically decreasing it. In order to recycle this fluid, a large portion of the water may need to be dried off to bring the density back into an acceptable range. This conventional process can be very time consuming and energy intensive.

Embodiments of the present invention can advantageously reduce the amount of time and energy required for recycle by giving a user the ability to separate the two waste streams (i.e., non-diluted fluid and rinse water). During an initial draw down portion of extraction, the waste fluid can be discharged via a recycle port. During the rinse portion of the cycle, the waste fluid can be discharged via a waste port. Keeping the fluids separate prevents the excess deionized water from diluting the higher-density fluid.

In general, embodiments of the present invention allow for a substantially continuous processing of samples. The samples can be automatically fed through the fractionation system 100. In this regard, the sample holders or sample racks 104 may be consistently spaced or indexed, or even connected in a continuous chain or loop (e.g., see FIGS. 25-28, 30, and 33). In some embodiments, each sample rack 104 can interface with a drive system 168, such as a drive sprocket or belt to move the sample racks 104. The drive system 168 can be driven via one or more drive motors. In some embodiments, an indexing feature or target can also be incorporated with each sample rack 104 that may be used for location detection. For example, the use of a visual target along with an optical sensor can allow for the fractionation system 100 and technicians to precisely locate/index sample tubes 106 and place the sample racks 104 directly under the extractor module 102.

Figure 30:
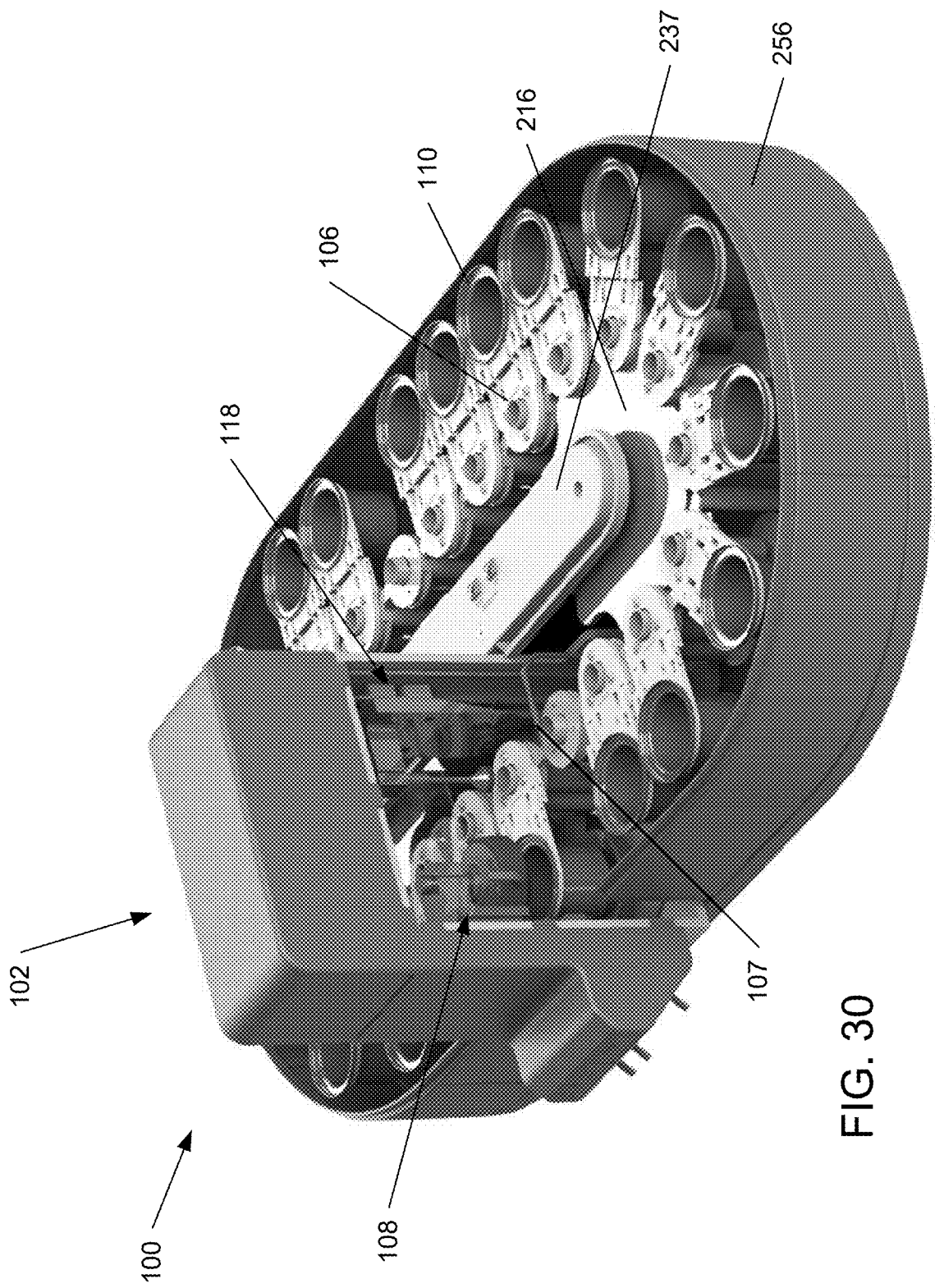
FIG. 30 is an isometric view of a fractionation system according to an embodiment of the invention.

In use, after the SOM light fraction and residual fluid has been removed from sample tube 106, the SOM heavy fraction and a small amount of know density fluid still remain in the sample tube 106. If the sample sits for a long duration, the water will begin to evaporate from the fluid, and the dissolved material used to modify fluid density will be left with the SOM heavy fraction. The addition of this material to the SOM heavy fraction can introduce error into mass measurements. To prevent this from occurring, the fractionation system can be equipped with a deionized water injection station. With reference to FIG. 30, this station, situated adjacent to the extractor location, can inject an amount (e.g., fixed or variable) of deionized water into each sample tube after the extraction has occurred. The water injection can be controlled via a valve (e.g., a solenoid valve). The amount of water injected can be a function of valve open time. A supply tube 107 is positioned directly above the sample tube 106 adjacent to the extractor location with a hole drilled radially into the tube which directs the fluid straight down. The end of the tube can be sealed, such as by being welded or plugged with an epoxy sealant, to ensure fluid can only travel downward into the tube.

Figure 6:
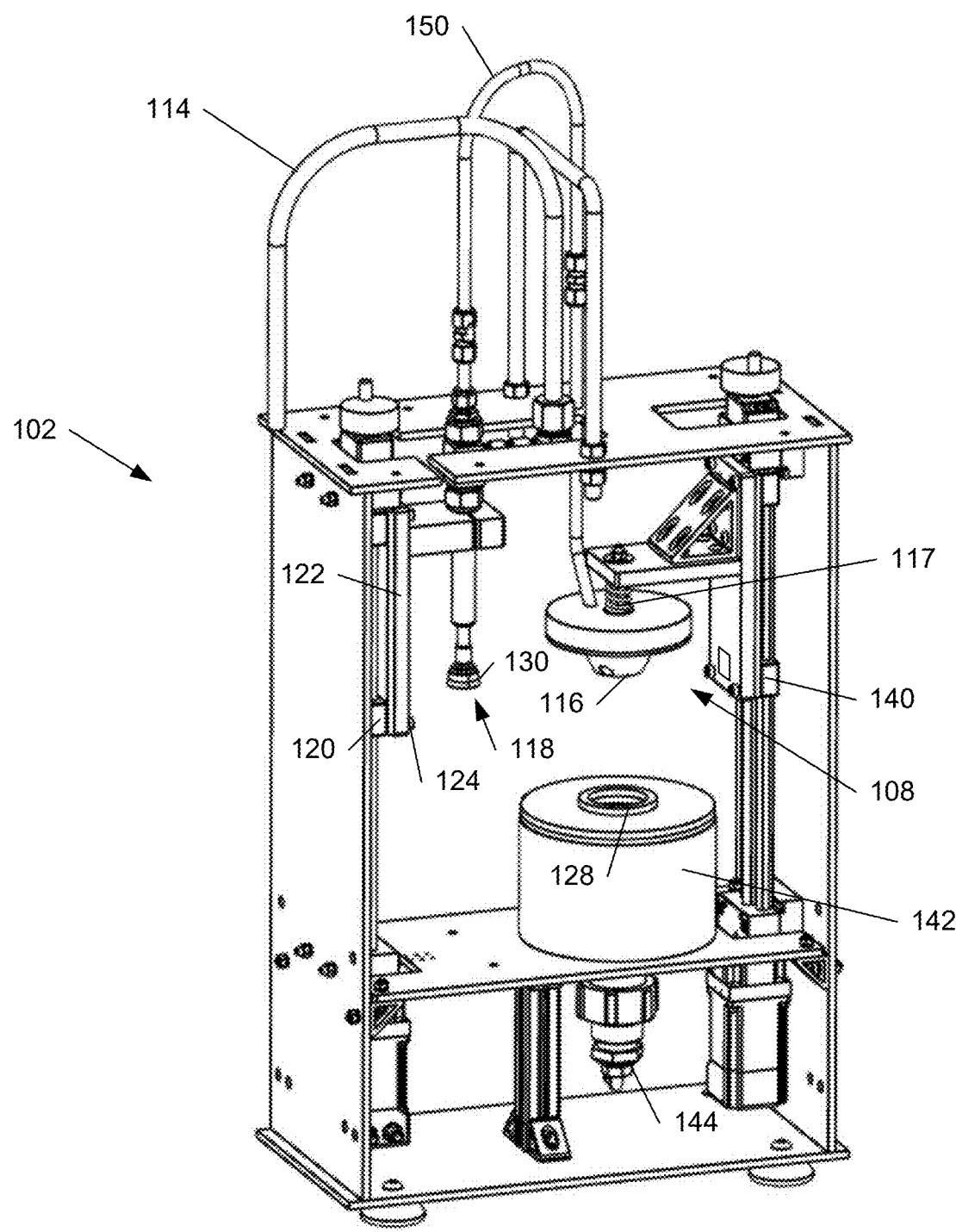
FIG. 6 is an isometric view of an extractor module of the fractionation system of FIG. 1.

FIG. 6 illustrates an embodiment of the extractor module 102. In some embodiments, the extractor module 102 can be a subassembly that can be inserted into, removed from, or independently maintained within the fractionation system 100. The extractor assembly 118 of the extractor module 102 can include the extractor nozzle 130 that can be inserted into a sample tube 106 to remove the soil organic matter light fraction. With additional reference to FIGS. 9 and 10, an insert tip 132 of the extractor nozzle 130 can include a cone geometry with a wide portion of the cone facing the sample tube 106. A conduit or hollow tube 134 can be connected to the insert tip 132 (e.g., at the narrow portion of the cone). A secondary cone-like structure 136, which may be configured generally as a solid cone in cross-section, may be situated within the larger cone insert tip 132, as shown, for example in FIGS. 9-16. The two cones 132, 136 can form an annular flow region or annular gap 138 at the bottom of the extractor nozzle 130 that is fluidly coupled to the hollow tube 134 to provide a flow path. The flow path can be used to extract soil organic matter light fraction. During an extraction, the vacuum chamber 142 can be in fluid communication with the tube 134 to create suction through the annular gap 138.

The extractor module 102 can further include tubing 150 that leads to the filter assembly 108. In use, fluid can travel through the flexible tubing 150 to bring the fluid to the filter assembly 108 where the fluid is injected into the filter cup 110 through the filter sealing member 116. In general, the plumbing (e.g., the tubing 150) of the extractor assembly 118 and the filter assembly 108 can be configured to eliminate or reduce the use of fittings that have the potential to retain material. For example, transitions that do occur between the flexible tubing 150 and the extractor assembly 118 may be located in a vertical run of the tubing with any raised edges pointing downward.

Figure 7:
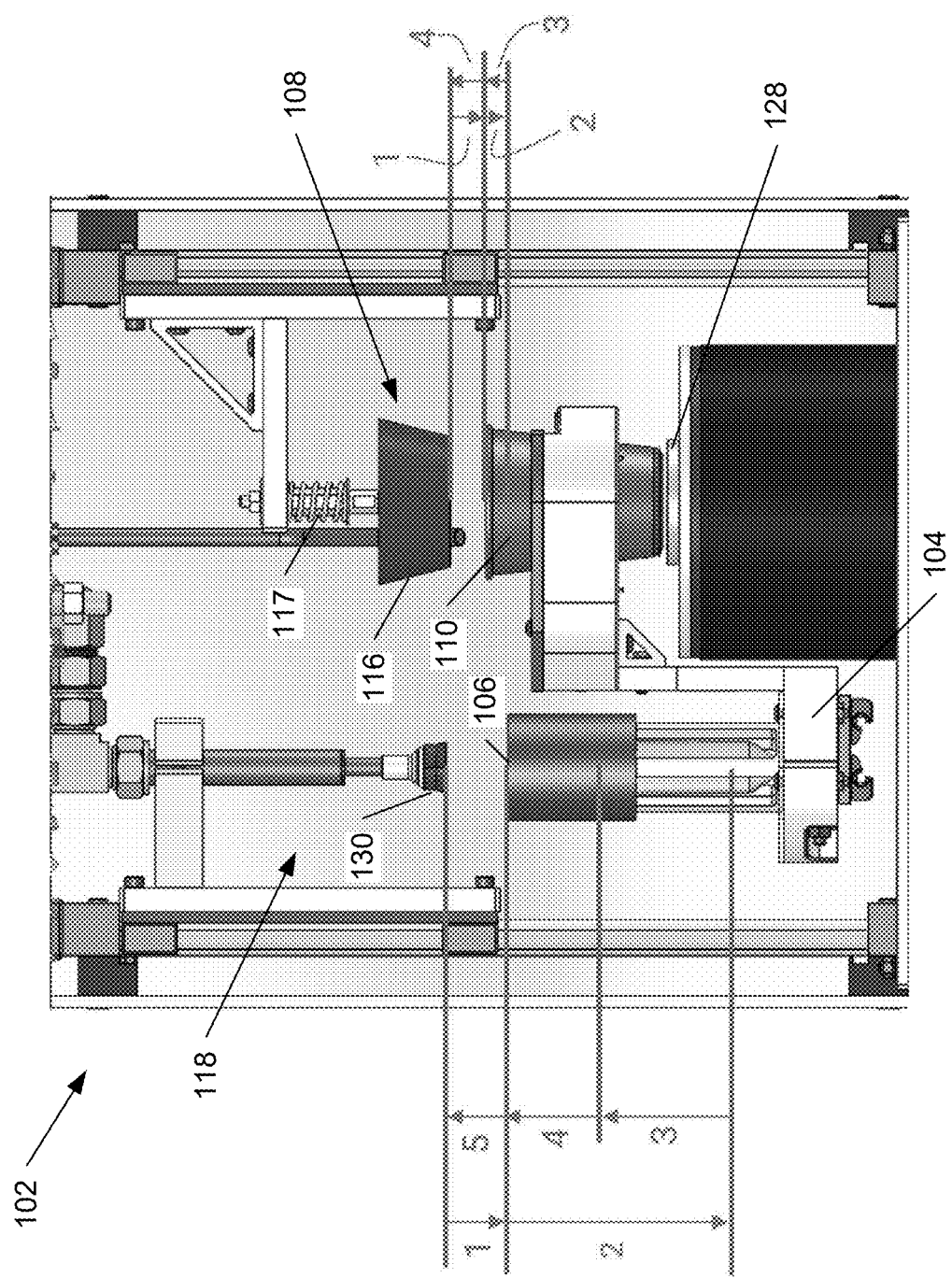
FIG. 7 is a side view of the extractor module of FIG. 6.

FIG. 7 illustrates the extractor module 102 and a sample rack 104 in position to have a sample extracted. Also shown in FIG. 7 are a series of positions that correspond to relative vertical positions of the filter sealing assembly 108 and the extractor assembly 118 during an extraction process. With reference to the filter assembly 108, in use, the filter assembly 108 can be moved toward the filter cup 110 to reach position 1. The speed at which the filter assembly 108 moves may be approximately 1.5 inches per second, however other operating speeds are possible via the linear actuator 140. The filter assembly 108 may spend approximately 0.8 seconds at position 1. As the filter assembly 108 moves to position 2, the filter sealing member 116 can engage the filter cup 110 (while also compressing the biasing member 117) to create a seal between the filter sealing member 116 and the filter cup 110 at the top of the filter cup and a seal between the filter sealing member 128 and the filter cup 110 at the bottom of the filter cup.

Once the extraction is complete, the filter assembly 108 can release the vacuum within the filter cup 110 by moving to position 3 and then the filter assembly 108 can be moved away from the filter cup 110 by moving to position 4. In some embodiments, the entire extraction process for a single sample rack 104 may take approximately 66 seconds, including moving the extractor assembly through positions 1-5 (discussed below) and moving the filter assembly through positions 1-4 (discussed above).

With reference to the extractor assembly 118, in use, the extractor assembly 118 can be moved toward the sample tube 106 to reach position 1. The speed at which the extraction assembly moves may be approximately 1.5 inches per second, however, other operating speeds are possible via the linear actuator 120. The extraction assembly 118 may spend approximately 1 second at position 1. As the extractor assembly 118 moves to position 2, an extractor nozzle 130 of the extractor assembly 118 can enter the sample tube 106 and extend through the light fraction. The extractor assembly 118 may spend approximately 23 seconds traversing to position 2 at, in one example, 0.2 inches per second. The extractor assembly 118 can then move (e.g., at 0.2 inches per second) to position 3 to provide a rinse sequence within the sample tube 106, as will be described in greater detail with reference to FIGS. 8A and 8B. The rinsing sequence or rinsing period may last approximately 15 seconds. The extractor assembly 118 can move to position 4 (e.g., at 0.2 inches per second) toward the top of the sample tube 106 and move (e.g., at 1.5 inches per second) from position 4 to position 5, at which point the extractor assembly 118 is removed from the sample tube 106 and the extraction may be complete.

Figure 8A:
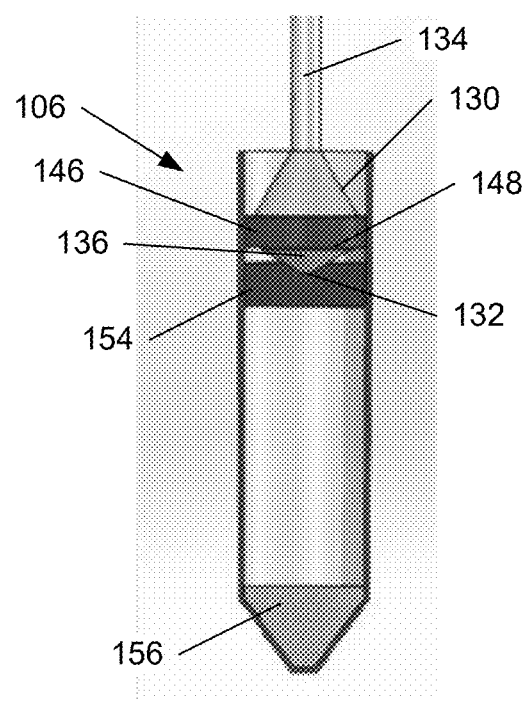
FIG. 8A is a side view of a sample holder and an extractor nozzle of the extractor module, the extractor nozzle in a first position.
Figure 8B:
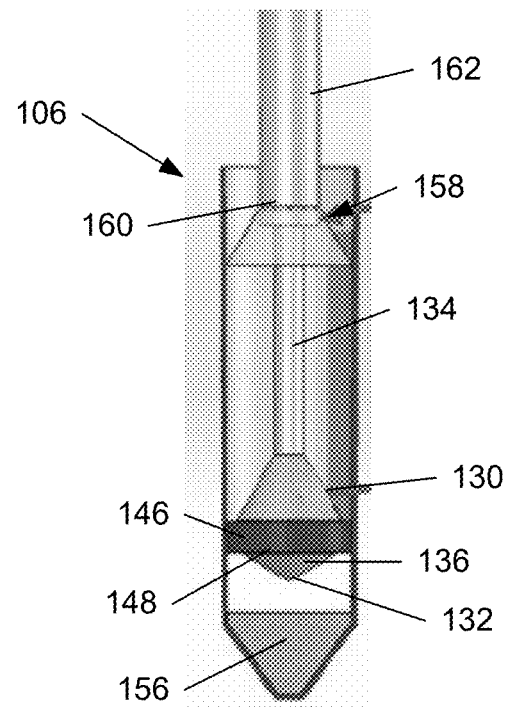
FIG. 8B is a side view of the sample holder and the extractor nozzle of the extractor module, the extractor nozzle in the second position.

As shown in FIGS. 8A and 8B, the extractor nozzle 130 can further include a wiper 146. The wiper 146 can be formed from a polymer material or other wiping or gripping material. The wiper 146 can include a leading edge 148. The leading edge 148 can be configured to remove a material that may be left behind on the inner wall (e.g., interior side wall) of the sample tube 106 during an extraction process as the fluid level drops within the sample tube 106. Since the leading edge 148 of the wiper 146 is adjacent to the annular gap 138 of the extractor nozzle 130, material on the inner wall of the sample tube 106 can get sucked up when a vacuum is applied.

The wiper 146 can also advantageously address or conform to a variety of sample tube 106 geometries, which may result from manufacturing or other processes. For example, in some embodiments, the sample tube 106 may be constructed from a molded plastic component. Due to some natures of manufacturing such components, the sample tube 106 may include a slight taper from the opening on one end toward the tip on the opposite end. Thus, in order to maintain contact with an inner wall of the sample tube 106 as the insert tip 132 travels down the sample tube 106 (i.e., away from the open end toward the closed end), the insert tip 132 can be flexible and allow for contraction (or other geometries). The wiper 146 on the outside of the insert tip 132 can include layers of material that contact the tube 106 wall with gaps in between or other flexible geometric features. This can allow for compression of the wiper 146 as the tube 106 narrows, thus establishing the desired wiping and sealing interface along the entire operational area of engagement.

With continued reference to FIGS. 8A and 8B, as well as additional reference to FIGS. 9-16, the secondary cone 136 can include a taper from the center out toward the annular region. In use, when a soil sample undergoes density separation via centrifugation, soil organic matter light fraction collects at the top of the column across the entire surface (see, for example, the light fraction 154 and the heavy fraction 156 of FIG. 8A). As the extractor nozzle 130 is inserted into the sample tube 106, the tapered tip of the secondary cone 136 can divert solids outward toward the annular gap 138, configured as an annular suction zone, to ensure all the materials are captured. In general, the internal geometry of the extractor nozzle 130 includes radii and corners with smooth transitions. This can reduce or eliminate locations where solid material can collect which can help ensure all materials are captured during an extraction process.

Figure 10:
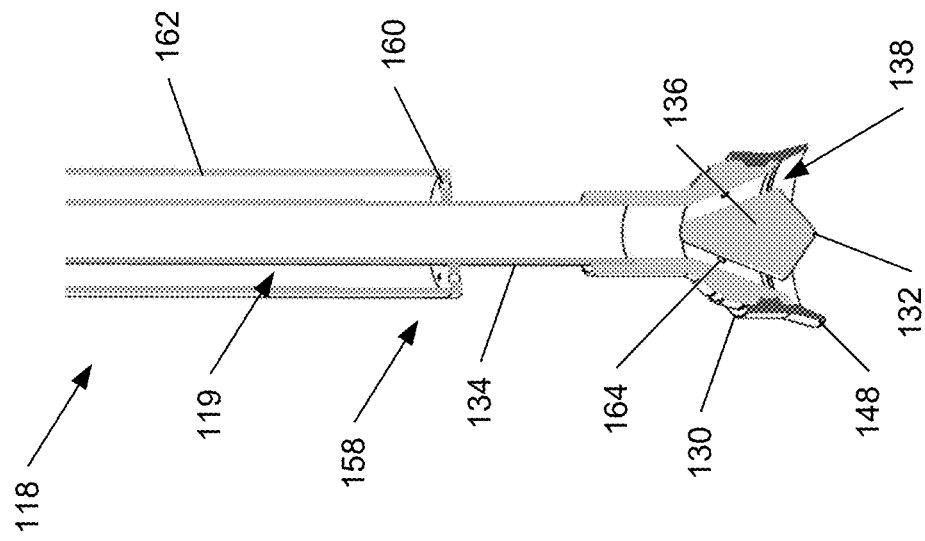
FIG. 10 is a side cross-sectional view of the extractor nozzle of FIG. 9.
Figure 9:
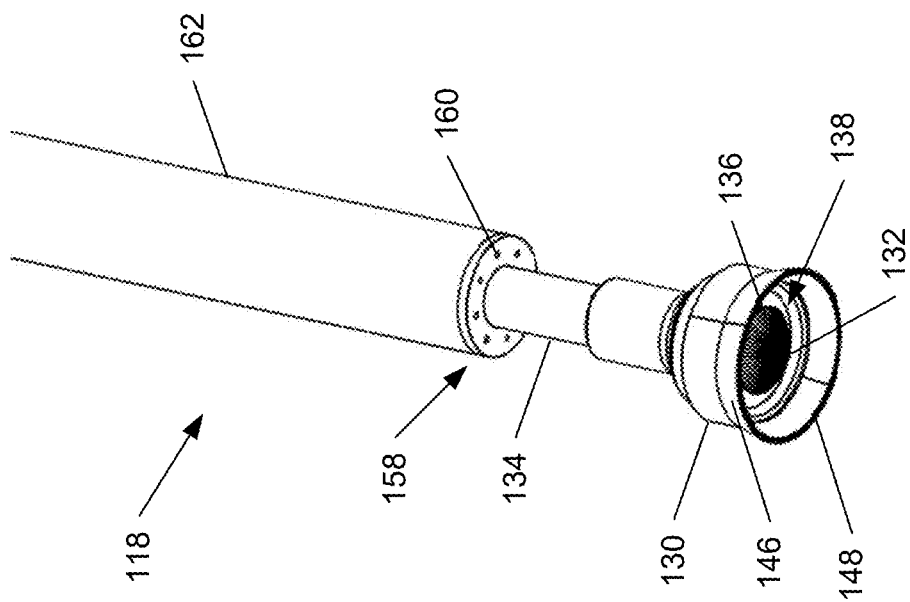
FIG. 9 is an isometric view of an extractor nozzle according to an embodiment of the invention.

Conventional methods of soil organic matter extraction can often leave behind residual material on inner walls of a sample tube (e.g., sample tube 106). The residual material may then be scraped off using a scraper. However, conventional scrapers can also leave behind dried material. Thus, embodiments of the invention can provide a secondary rinse system 158 that can inject liquid (e.g., deionized water) into the sample tube 106 after the insert tip 132 has been inserted into the tube 106 and, in some embodiments, after the majority of the light fraction has been extracted. The rinse system 158 can be located axially above the insert tip 132 and can be configured to rinse an inner wall of the sample tube 106 by injecting fluid around its parameter through a series of holes 160 (or other openings) formed (e.g., drilled) into a secondary annular tube 162 of the extractor nozzle assembly (see, for example FIGS. 9 and 10). The series of holes 160 can be angled downward (e.g., as shown in FIGS. 9 and 10) or radially outward (e.g., as shown in FIG. 8B) to urge fluid and materials through the insert tip 132 and to prevent splashing of fluid out of the tube 106. The rinse fluid can be supplied via a rinse conduit/tubing 114 plumbed with the extractor nozzle 130 via a manifold 115 (see FIG. 4). The rinse fluid is directed through the cylindrical chamber 119 between the tubes 134, 162 (see FIG. 10) toward the holes 160.

With reference to FIGS. 9-16, and in particular, FIGS. 10 and 13, in order to collect rinse fluid and any residual material, an array of holes 164 can be formed in the insert tip 132 (e.g. an outer wall of the extractor nozzle 130). The array of holes 164 can be in fluid communication with the annular gap 138 via sidewall channels 166. Fluid that is injected above the insert tip 132 is directed, via an annular gutter 167, and sucked up though the same flow cavity as the rest of the subject fluid in the sample tube 106. In general, FIGS. 9-16 illustrate a comparison between a variety of example geometries of the extractor assembly 118. In general, the total flow area of the array of holes 164 is significantly smaller than the total flow area of the annular gap 138 that forms the annular flow region of the extractor nozzle 130. For example, the ratio of the total flow area of the annular gap 138 to the total flow area of the array of holes 164 is approximately 10:1.

Figure 17:
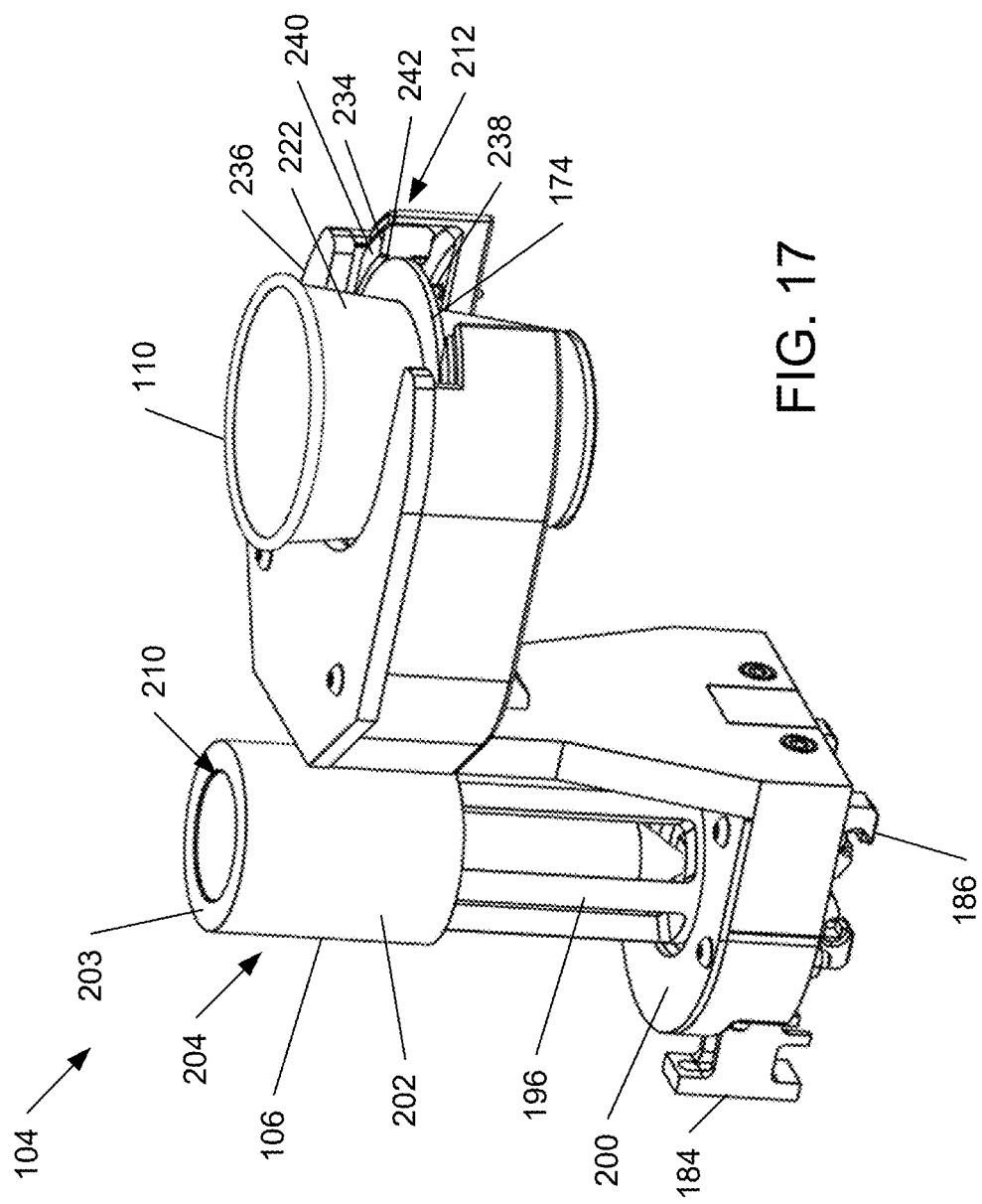
FIG. 17 is an isometric view of a sample rack of the fractionation system of FIG. 1.
Figure 18:
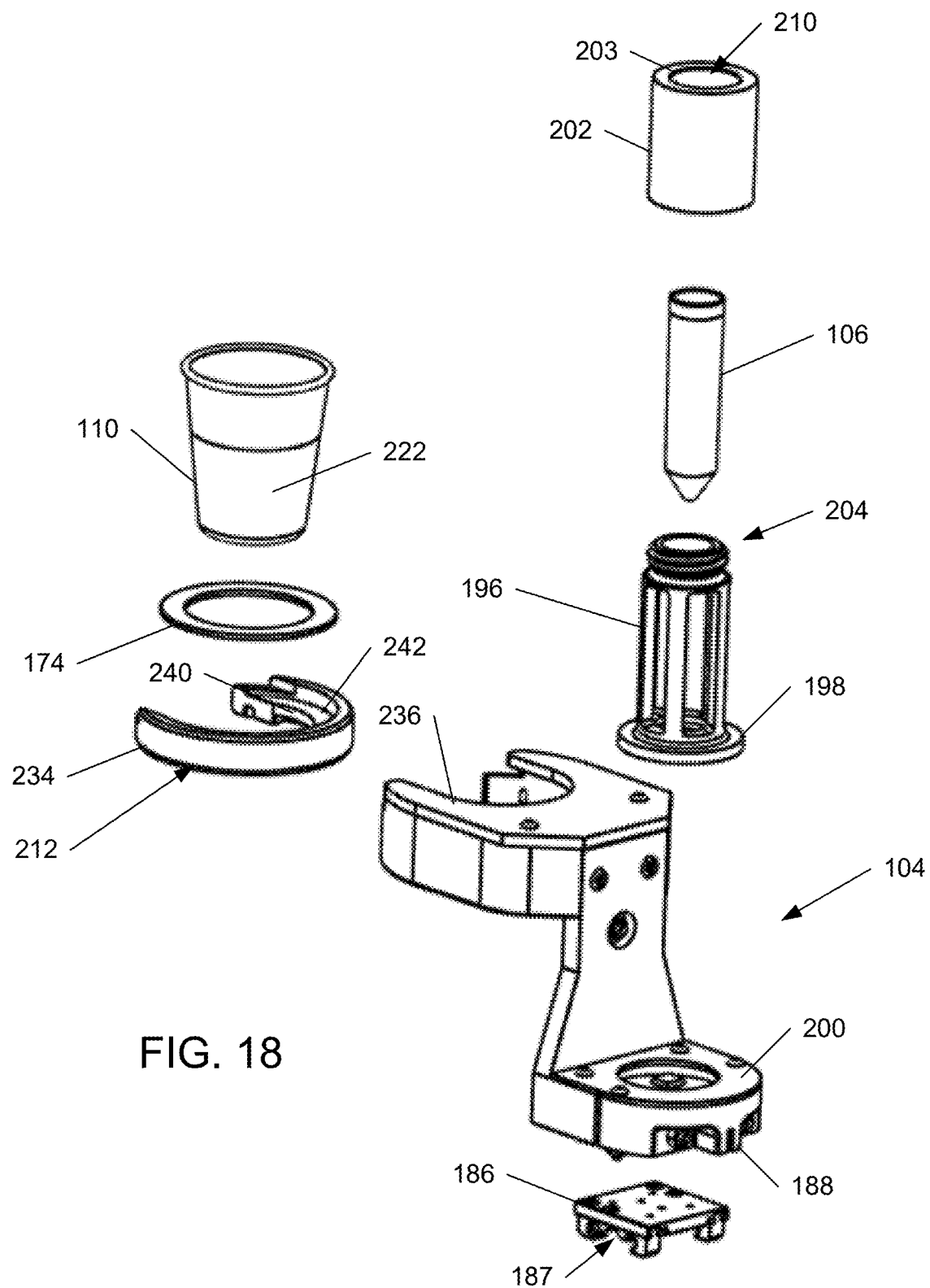
FIG. 18 is a partial exploded isometric view of the sample rack of FIG. 17.

As shown in FIGS. 17 and 18, the sample tube 106 and the filter cup 110 are combined in the sample rack 104. The sample rack 104 can keep the sample tube 106 and the filter cup 110 physically connected as they travel through the fractionation system 100. In some embodiments, the sample tube 106 can be inserted into a primary opening 210 of the sample rack 104. The sample tube 106 is seated within a cylindrical cage 196 having a lower flange 198 captured beneath a base plate 200. An upper alignment sleeve 202 (as shown in FIGS. 5, 17, and 18) is secured to the upper end 204 of the cage 196. The alignment sleeve 202 (defining the primary opening 210) may include an internal tapered surface 203 to help aid alignment of the extractor nozzle 130 into the tube 106. That is, the primary opening 210 is larger than the opening of the tube 106, and the internal tapered surface 203 of the alignment sleeve 202 transitions from the larger opening size to the smaller opening size.

A filter cup holder 212 can secure the filter cup 110 relative to the sample tube 106. The sample rack 104 as an assembly can also include a floating flange 174 that is secured relative to the filter cup 110. In some embodiments, the flange 174 is fixed to the filter cup 110. In this regard, in some embodiments, the flange 174 can be integrally formed with the filter cup 110. The floating flange can be held by the filter cup holder 212. The floating flange 174, and thus the filter cup 110, can move radially and axially with respect to the filter cup holder 212. This slight amount of available movement can help center the filter cup relative to the filter sealing assembly 108 of the extractor module 102 and allow some vertical give when the filter sealing member 116 is pressed against the top of the filter cup 110.

In general, the floating flange 174 can facilitate the formation of a vacuum within the filter cup. In addition, the filter cup holder 212 can be configured to include a C-shaped ring 234 that, when captured beneath an upper plate 236, is urged toward the upper plate 236 by one or more biasing members 238 (e.g., helical spring, resilient member). In one embodiment, the C-shaped ring 234 includes a beveled interface 240 that cams with the flange 174 during insertion of the filter cup 110. Also, the biasing members 238 can provide additional compressive force and positional adjustability when the filter cup 110 is engaged with the filter sealing member 116.

In use, the biasing members 238 can compress when the first sealing member 116 comes in contact with the top of the filter cup 110. When the biasing members 238 are compressed, the filter cup 110 is allowed to move downward and create a seal with the bottom sealing member 128 below. This compliancy can allow the filter cup 110 to be sealed at the top and bottom while only moving one of the two sealing members 116, 128. The C-shaped ring 234 can also include a ledge 242 with a diameter that is larger than the diameter of the flange 174 so that the flange 174 (and hence filter cup '110) can accommodate axial and lateral misalignment during engagement between the filter cup 110 and the sealing member 116.

Figure 19:
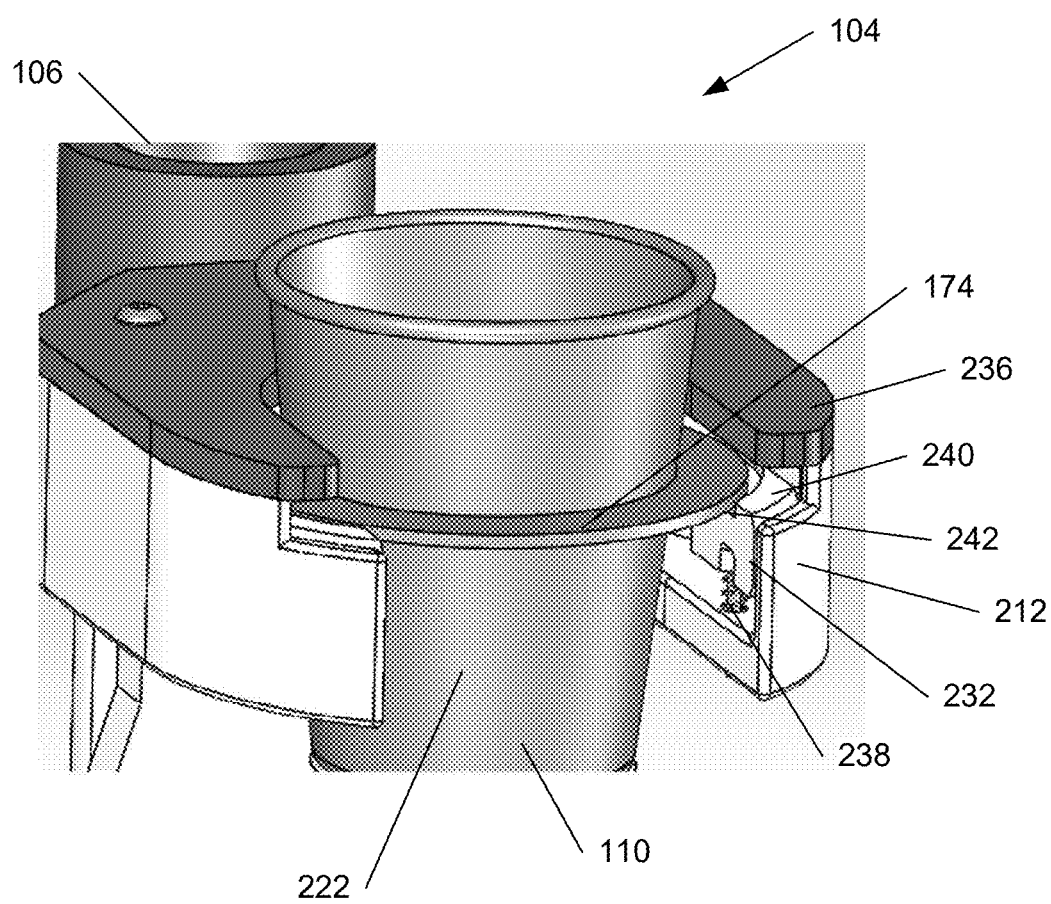
FIG. 19 is an isometric view of a filter cup held by the sample rack of FIG. 17.
Figure 20:
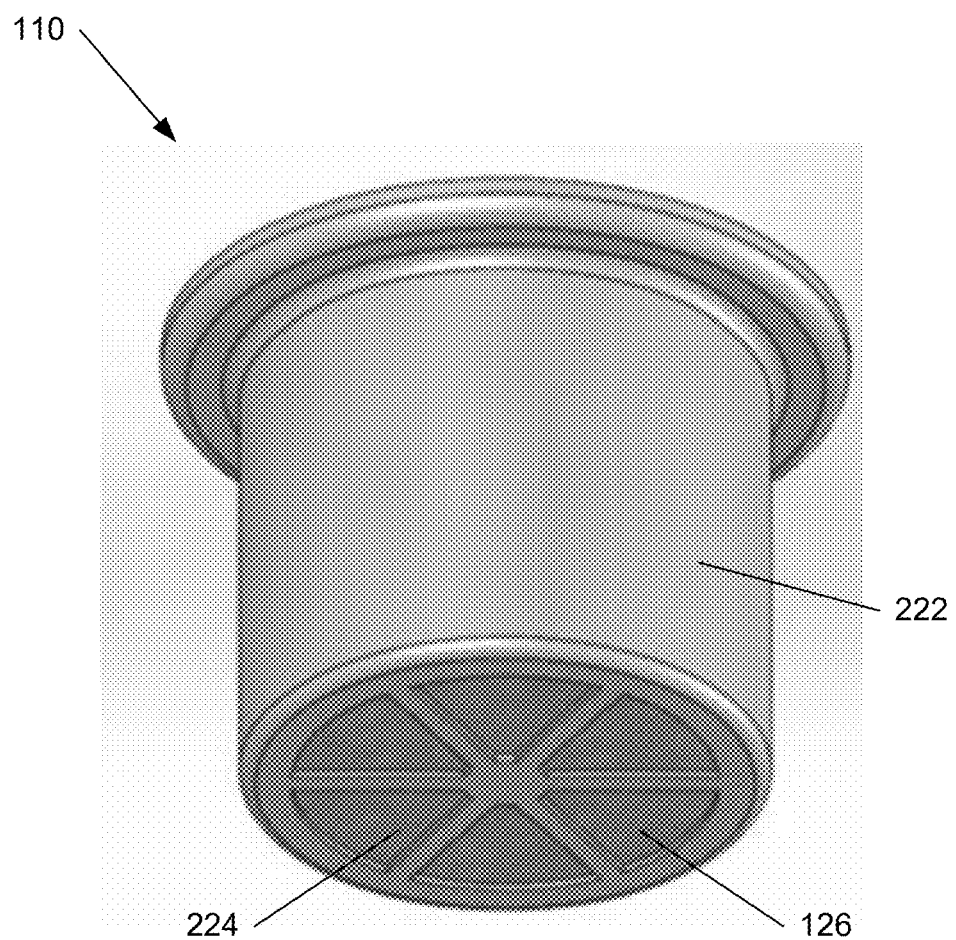
FIG. 20 is a bottom isometric view of the filter cup of FIG. 19.

FIGS. 19 and 20 illustrate different embodiments of the filter cup 110. In particular, FIG. 19 illustrates the filter cup 110 according to one embodiment of the invention. Some conventional methods of soil fractionation may use an individual filter paper to collect samples. However, the filter cup 110 of the present invention can provide a more secure, robust, and reliable vessel for collecting samples when compared to conventional filter papers. The filter cup 110 can include a filter cup body 222 and a mesh base 224 that provides a screen at the bottom of the filter cup 110. In some embodiments, the filter cup body 222 and/or the mesh base 224 can be formed from metal.

As shown in FIG. 20, in some embodiments, a top of the filter cup 110 can include a flat horizontal section followed by a smooth rounded transition into the cup. The flat portion can allow the cup 110 to be held via gravity in a ring of a sample rack 104. The transition into the cup can be smooth or otherwise rounded with a smooth surface finish that can allow a rubber sealing piece (e.g., the sealing member 116) to create a seal around the circular perimeter of the top of the cup 110. The walls of the cup 110 in the illustrated embodiment can be straight vertical sides or tapered sides that transition to the bottom via a smooth rounded transition. The external surface of the bottom of the cup 110 can have a smooth surface finish, similar to the top edge, that can allow a sealing member (e.g., the filter sealing member 128) to form a seal with the bottom of the filter cup 110.

In the illustrated embodiment, a metal mesh 224 covers a majority of the bottom of the cup 110. In some embodiments, the metal can be configured as a 20 micron mesh size. The mesh can be bonded to the cup 110 via a welding or adhesive. An epoxy can be used along the boundary between the cup 110 and a filter 126 to create a smooth transition and eliminate any potential for capturing materials. In this regard, only the filter 126 advantageously collects the extracted sample matter.

Generally, in order to generate suction to pull fluid out of the sample tube 106, a vacuum must be applied to the filter cup 110. The filter sealing assembly 108 can be configured to compress a flexible rubber gasket (e.g., the sealing member 116) on the top and bottom of the filter cup 110 to create a sealed chamber. As briefly described above, the filter sealing member 116 can include a taper geometry and may generally be shaped like a rubber flask stopper. The top seal 116 can be connected to the linear actuator 140 that can move in the vertical direction, similar to the linear actuator 120 for the extractor nozzle 130. As the actuator 140 moves downward, it presses the top seal 116 into the top of the filter cup 110, thereby creating a seal. The bottom seal 128 can include a cone-shaped rubber gasket mounted on top of the vacuum chamber 142. In some embodiments, as the actuator 140 moves downward, both the top and bottom seals 116, 128 are compressed against the filter cup 110 to complete a sealed vacuum chamber.

Figure 21:
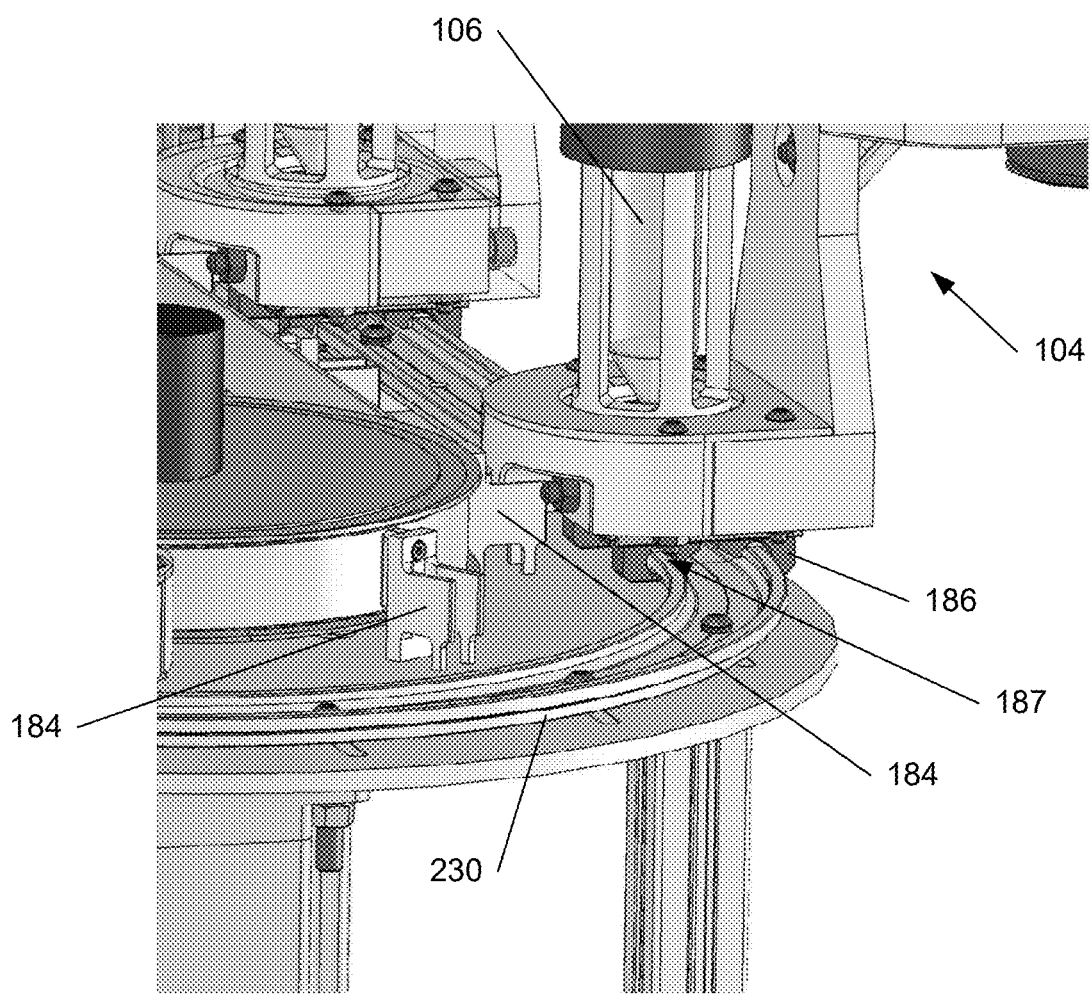
FIG. 21 is an isometric view of a carriage of the sample rack along a track of the fractionation system of FIG. 1.

As shown in FIG. 21, each sample rack 104 can include a drive connector 184 to link and index the sample rack 104 to the drive system 168. In the illustrated embodiment, the drive connector 184 is secured relative to a belt of the fractionation system 100 to move each sample rack 104 along the oval-shaped track 230.

Figure 22:
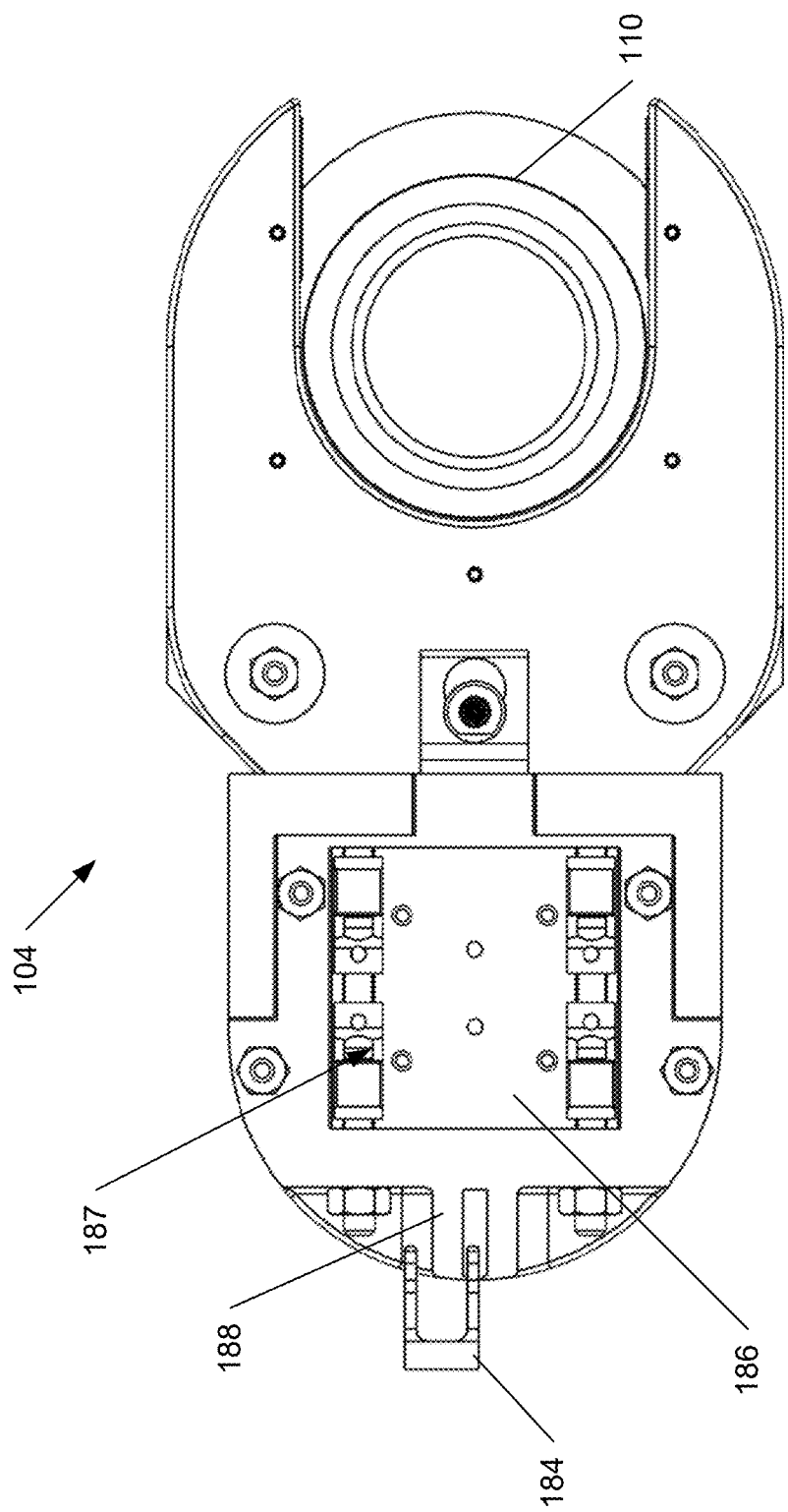
FIG. 22 is a bottom view of the sample rack of FIG. 17.

FIG. 22 illustrates a bottom view of the sample rack 104 including the drive connector 184. In the illustrated embodiment, the drive connector 184 is generally configured as a C-shaped or two-pronged clip that engages a driven connector 188 in the bottom of the sample rack 104. The driven connector 188 can also take the form of parallel plates or fingers sized to engage with the drive connector 184. In addition, the placement interface between the example drive connector 184 and the example driven connector 188 provides a predetermined relative spacing between adjacent racks 104. The engagement of the drive connector 184 with the driven connector 188 of the sample rack 104 allow for radial movement between the drive connector 184 and the sample rack 104. For example, as the drive connector 184 drives a sample rack 104 around the track 230, the sample rack may move radially outward or inward relative to the drive belt as the sample rack 104 rounds a corner. The rack 104 includes a trolly plate 186 defining channels 187 configured to ride along the track 230 while retaining the rack 104 to the track 230.

Figure 23:
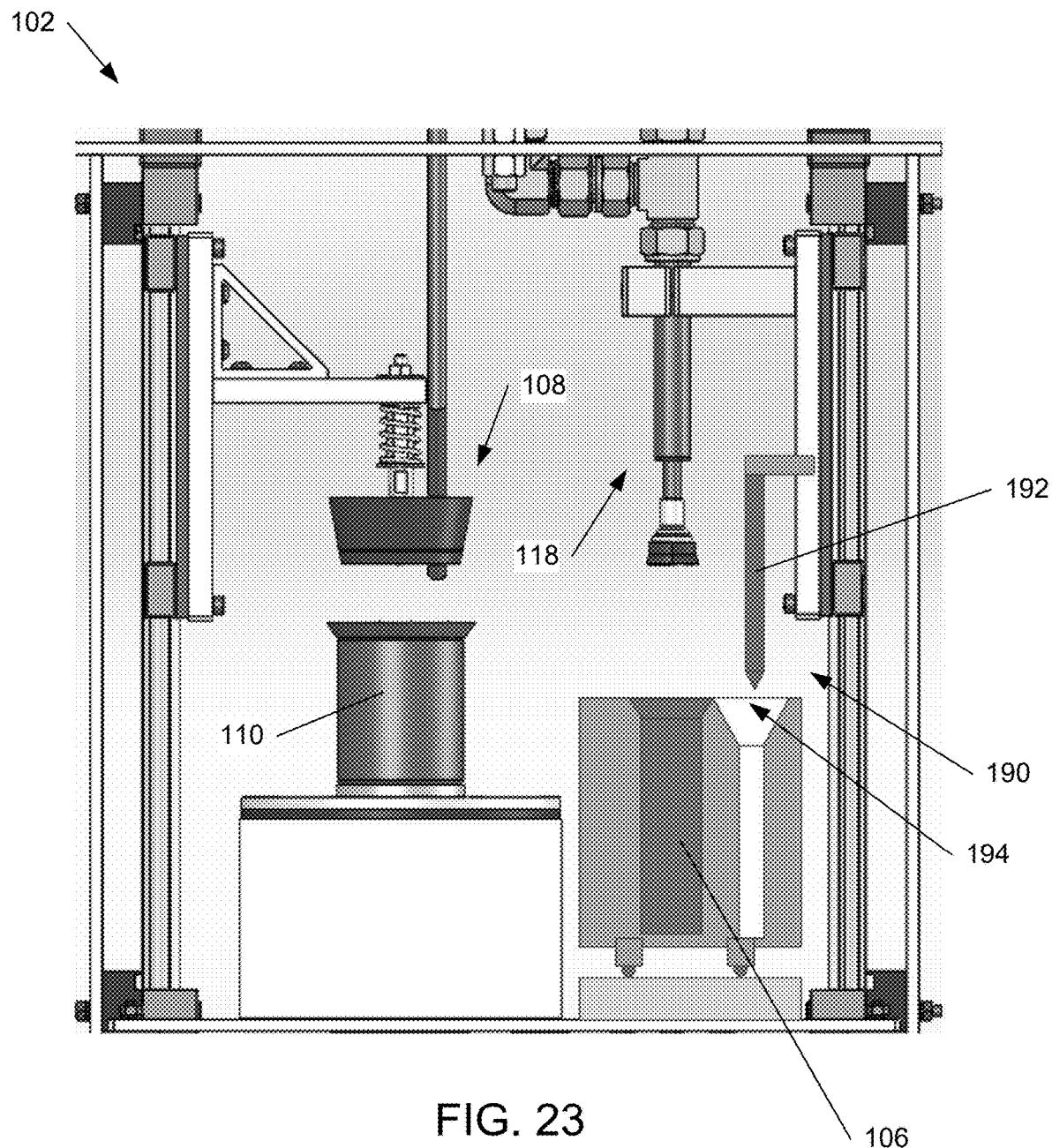
FIG. 23 is a side view of the extractor module including an indexing system according to an embodiment of the invention.
Figure 24:
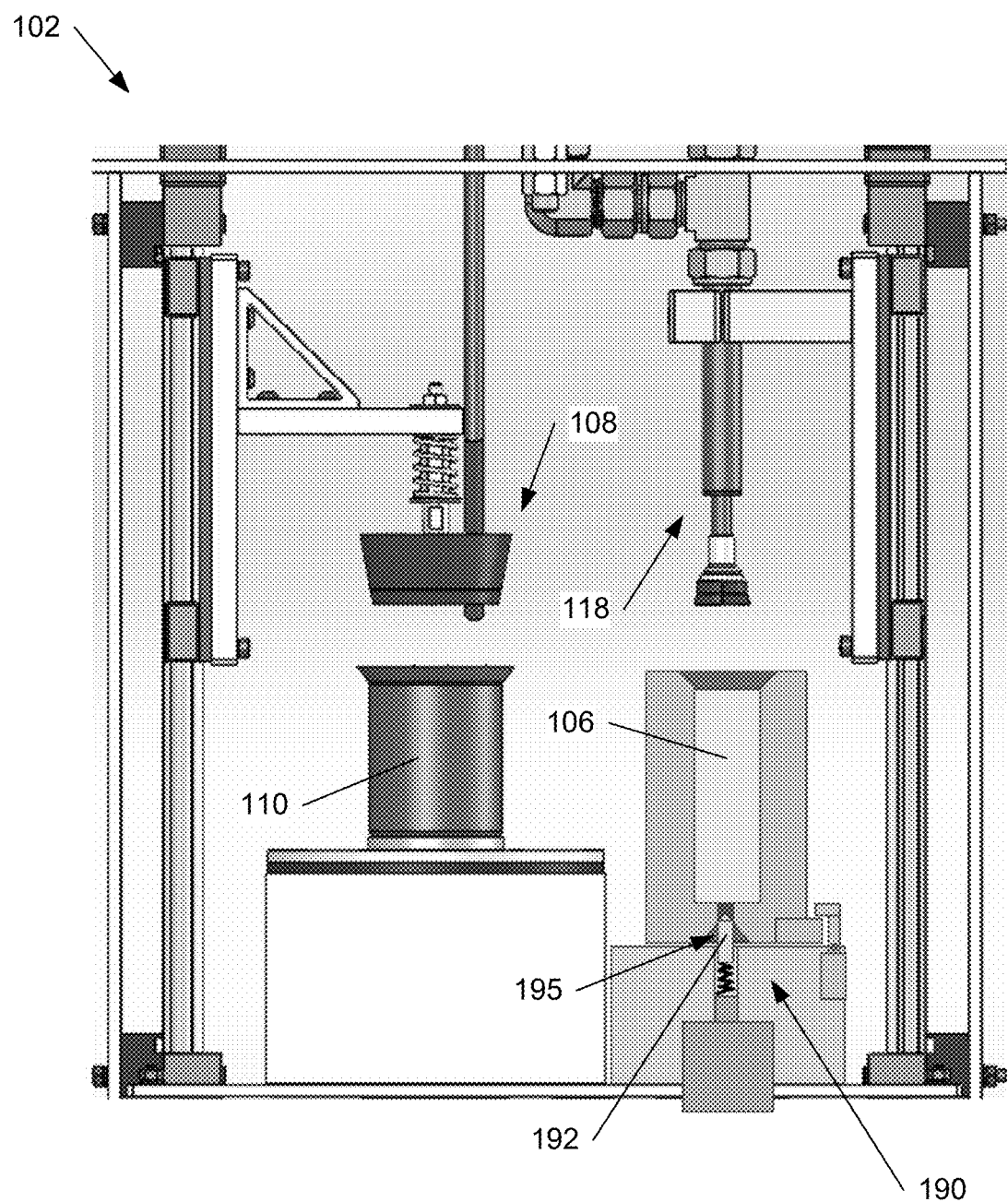
FIG. 24 is a side view of the extractor module including an indexing system according to another embodiment of the invention.
Figure 25:
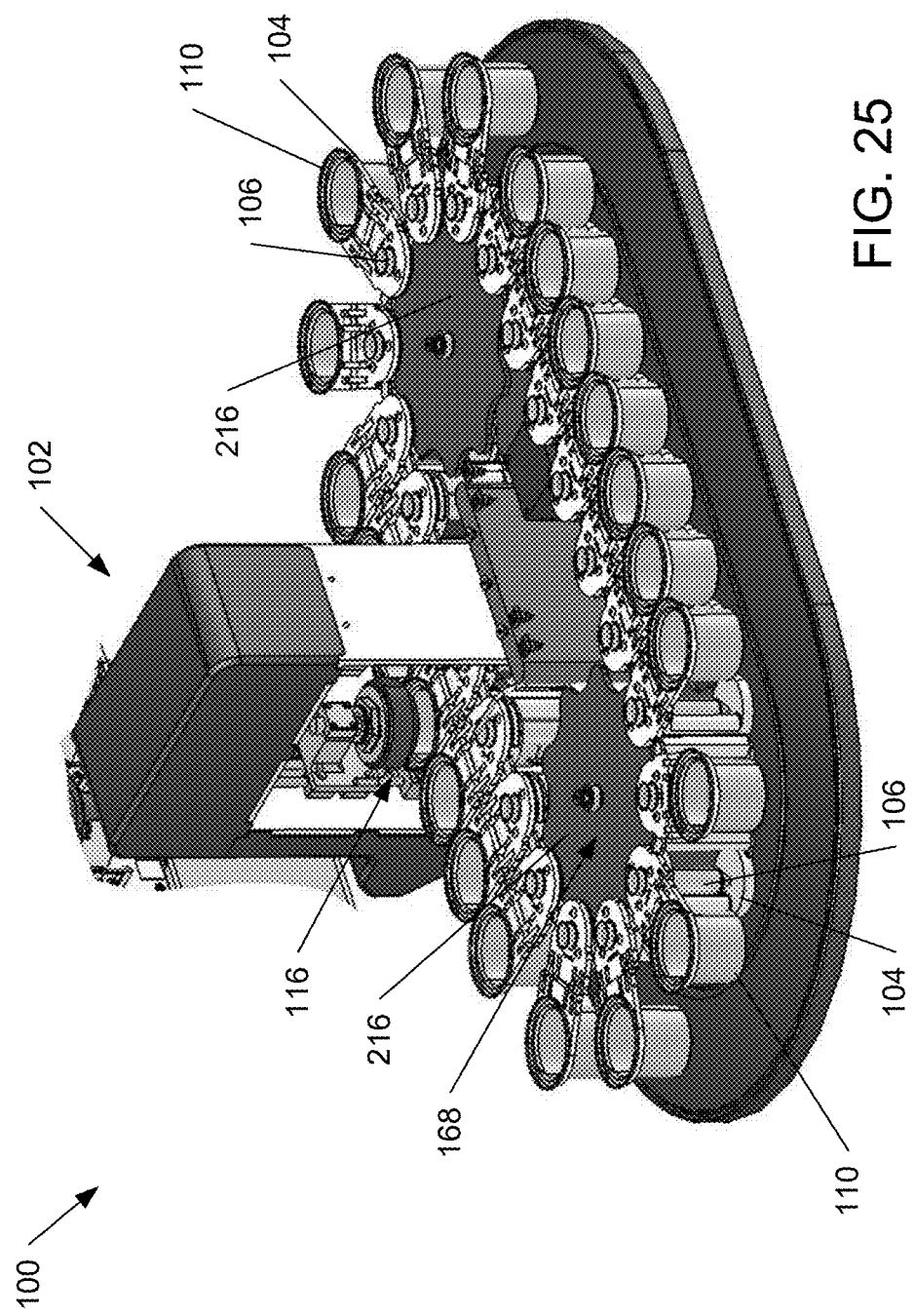
FIG. 25 is an isometric view of a fractionation system according to an embodiment of the invention.

FIGS. 23 and 24 each include embodiments of an indexing system 190. The indexing system 190 can be used to index, label, organize, or position any sample rack 104 relative to the extractor module of the fractionation system. In general, the indexing system 190 can include a first indexing member that is stationary relative to the extractor module 102 and complementary indexing members disposed on each of the plurality of sample racks 104, filter cups 110, or sample tubes 106. With reference to FIG. 23, the indexing system 190 can include a pin 192 (e.g., a first indexing member) generally configured to be received by an opening 194 (e.g., a complementary indexing member) in the sample rack 104. In the illustrated embodiment, the opening 194 can include a tapered opening that allows for self-centering as the pin 192 is inserted into the opening. For example, if the pin 192 is not directly axially aligned with the opening, the tapered opening 194 can correct for axial misalignment and facilitate aligning the pin 192 within the opening 194 as the pin 192 enters the opening 194. In this example, the sample rack 104 may be slidably mounted (e.g., such as on pin rollers or a track, similar to track 230).

With reference to FIG. 24, the indexing system 190 can similarly include a pin 192 (e.g., a first indexing member) generally configured as a detent. The pin 192 can engage a complementary index feature 195 (e.g., a recess, opening, or dimple) in the sample rack 104. In the illustrated embodiment, the opening in the sample rack 104 is formed beneath the sample tube 106, however, other orientations are possible. For example, the pin 192 could engage another area or surface of the sample rack 104, such as adjacent to the filter cup 110

FIGS. 25-30 illustrate other embodiments of a drive system 168 according to embodiments of the invention. In the illustrated embodiment, each sample rack 104 can include a drive connector 184 that is configured to interface with drive sprockets 216. In some embodiments, this interface can exist on both a top and bottom of the sample rack 104. In the illustrated embodiment, the drive system 168 can include a large sprocket 216 that can interface with both the top and bottom drive connectors 184 of the sample racks 104. A pair of sprocket assemblies can be used to maintain chain tension in the sample chain of racks 104. At least one of the sprockets 216 can be connected to a drive motor 218 via a belt 220 that turns the sprocket 216. An opposite sprocket 216 can be a driven sprocket that is not powered but used to maintain tension on the chain of racks 104.

In some embodiments, two of the sprockets can be mounted to a bottom plate 235 and can be isolated via bearings that allow them to rotate freely. The tops of the sprocket can be connected via a top plate 237 that can prevent them from flexing toward each other when belt tension is applied. The mounting features on the top plate 237 and the bottom plate 235 for the drive sprocket 216 can be slotted to allow the sprocket to be moved slightly to tension the chain. The top plate 237 may also be connected to the bottom plate 235 via a vertical member that provides stability to the assembly. The drive motor 218 can be mounted on the bottom plate 235 and interfaces with the bottom of the shaft of the driven sprocket assembly via belt 220 in the illustrated embodiment.

As briefly described above, the sample racks 104 can include an additional feature that is used to detect the presence of the rack 104 when it enters the area of the extractor module 102. The extractor module 102 can include a sensor (e.g., optical, ultrasonic, hall effect) capable of detecting a particular target/structure/feature. For instance, as the sample chain moves into the extractor area, an optical position sensor can detect a target on the sample rack 104 and signal to the control system to stop motion of the chain. After the sample has been extracted, the system can move the chain again until the next sample enters the extraction area.

Figure 27:
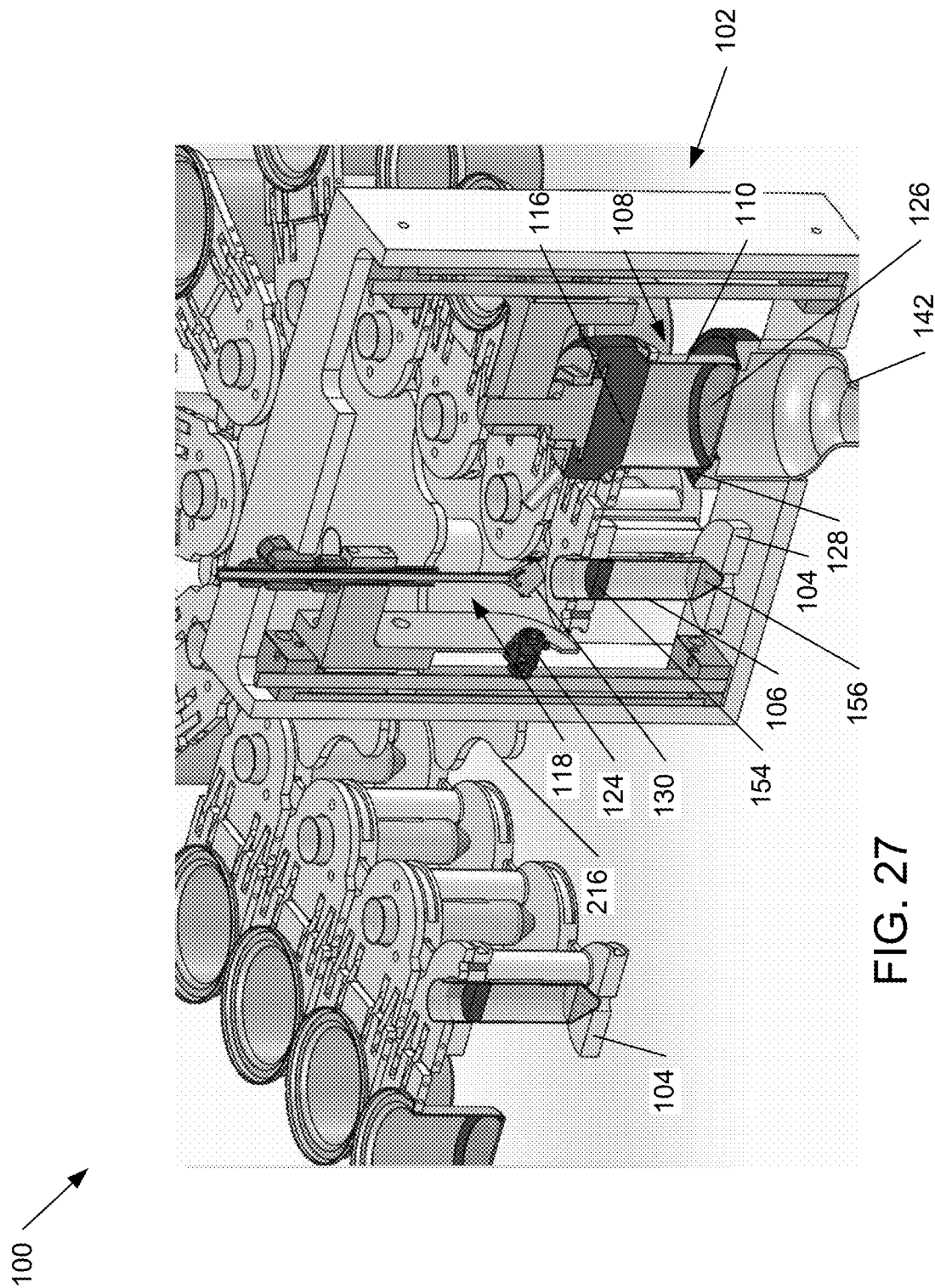
FIG. 27 is an isometric cross-sectional view of the fractionation system of FIG. 25.

FIG. 27 illustrates another embodiment of the fractionation system 100 and the extractor module 102. The fractionation system 100 includes a plurality of sample racks 104 each having a sample tube 106 and a filter cup 110. The sample tube 106 is configured to engage with the extractor assembly 118 and the filter cup 110 is configured to engage with the filter assembly 108. A set of tubing (not shown in FIG. 27) can fluidly couple the extractor assembly 118 and the filter assembly 108. The filter assembly 108 can also be in fluid communication with the vacuum 142. The vacuum chamber 142 can be in fluid communication with rinse fluid and a waste trap to collect waste fluid. In addition, a sensor 124 is provided to aid the relative movement of the extractor assembly 118 and the sample tube 106 during extraction.

Figure 28:
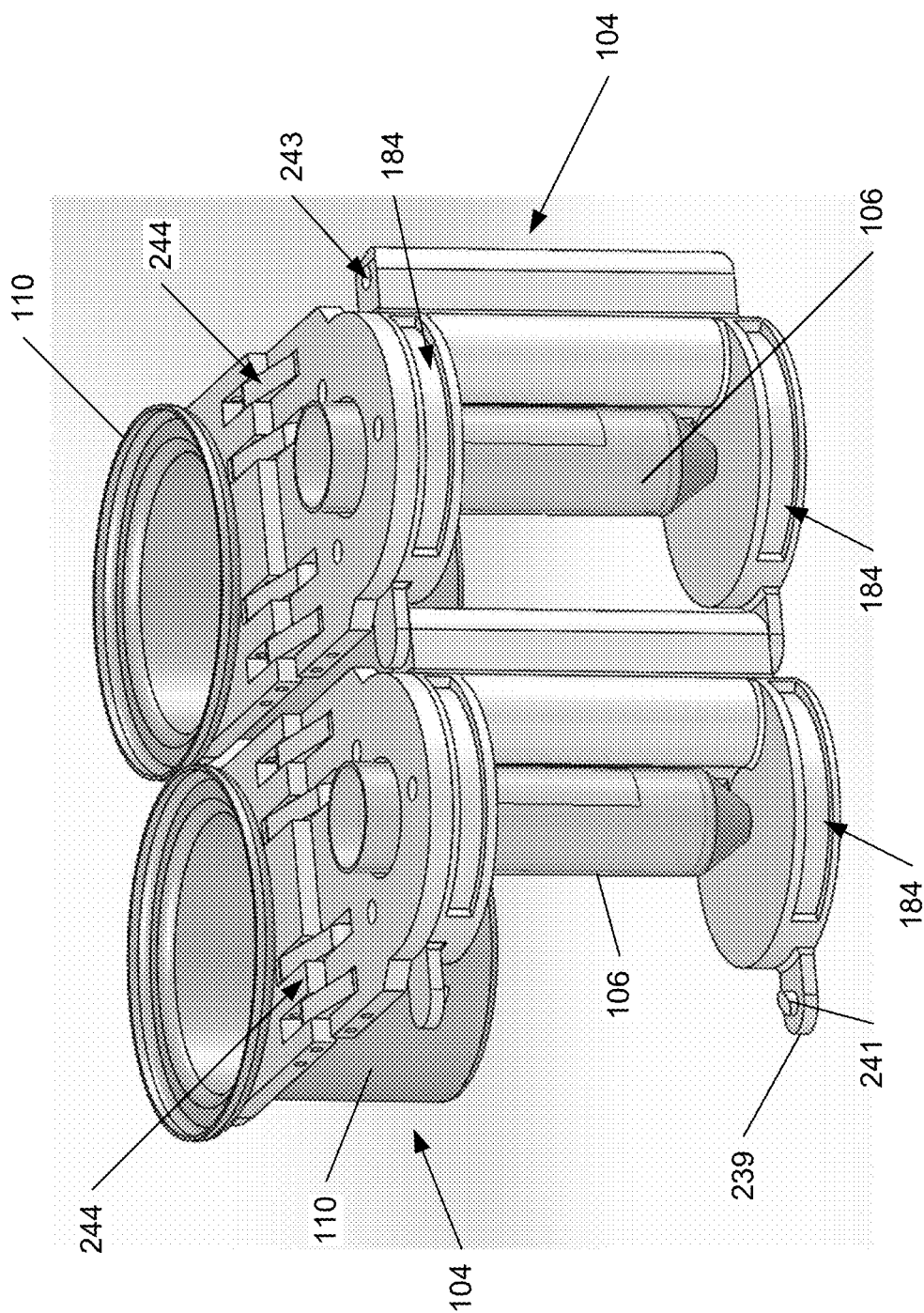
FIG. 28 is an isometric view of two sample racks of the fractionation system of FIG. 25.
Figure 29:
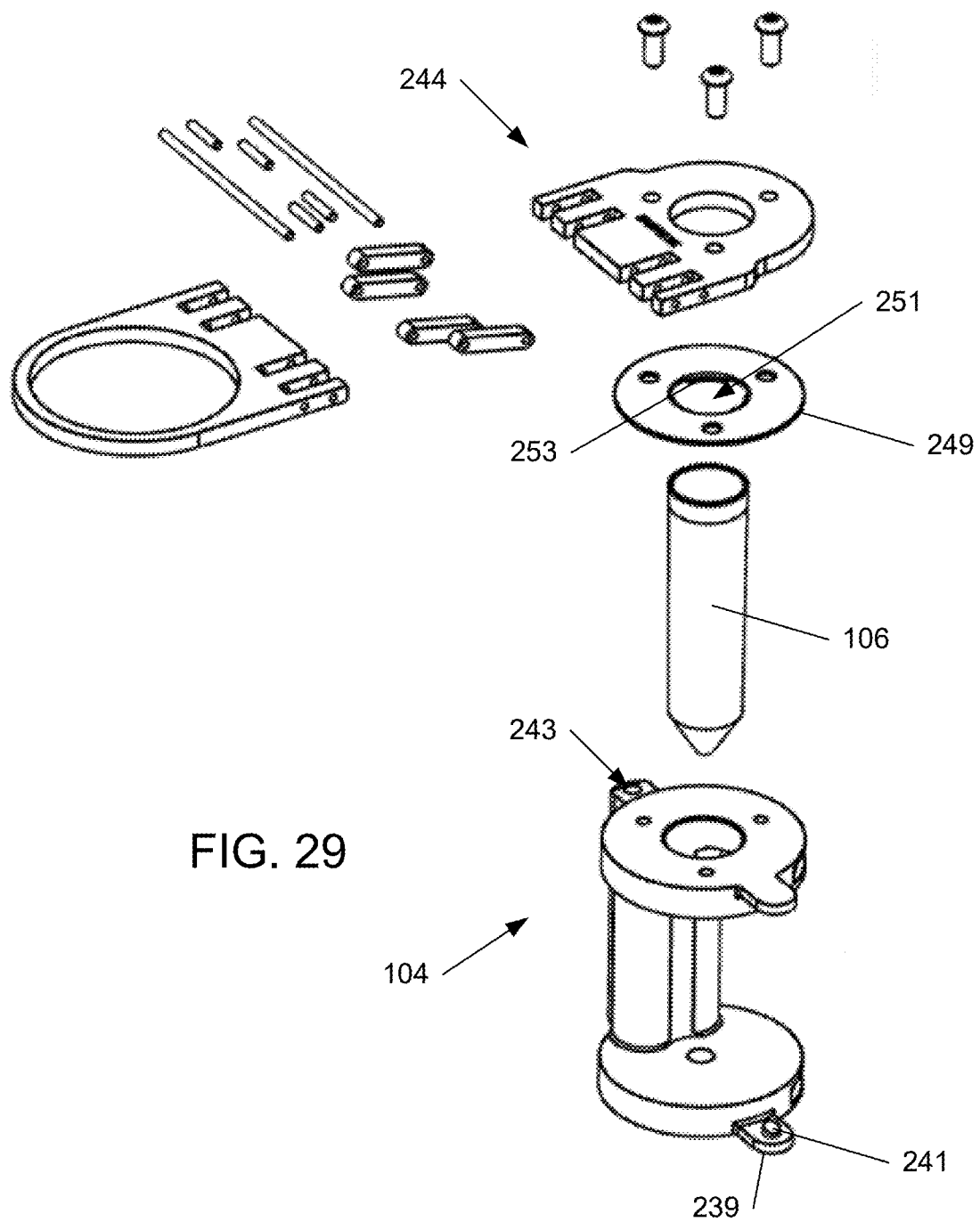
FIG. 29 is an exploded isometric view of one sample rack of FIG. 28.

As shown in FIGS. 28 and 29, some embodiments of the sample rack 104 can include a pivoting section 244 between the sample tube 106 holder and the filter cup holder 212. The linkage of the pivoting section 244 can allow the top of the pivoting section 244 to remain parallel to the surface of the holder 104 as it pivots up and down during operation. When the rack 104 is positioned within the extractor module 102 and the filter cup 110 seated against the seal 116, the relative positioning of the surfaces generally swap, while again maintaining the parallelism. The pivoting section 244 can be spring biased to be held in its upper position. In this position, the surface of the pivoting section may be roughly 0.5 inches above the adjacent surface of the rack 104.

As briefly described above, in use during operation, a top seal (e.g., the seal 116) can press on the top of the filter cup 110. The downward motion can push the filter cup 110 downward into a bottom seal (e.g., the seal 128). This can allow the vacuum chamber 142, to which the bottom seal 128 may be connected, to remain stationary relative to the sample rack 104.

In some embodiments, each holder or sample rack 104 can include a unique marking on top. This can allow a technician that loads and unloads samples into the fractionation system 100 to identify the samples via a unique identifying character. Additionally, with reference to FIG. 29, in some embodiments, sandwiched between a primary holder and the pivoting holder 104 can be a thin rubber or generally pliable sheet/membrane 249. The rubber or pliable sheet/membrane 249 can include an opening 251 that aligns with the sample tube 106 holder and has a plurality (e.g., three) radial tabs 253 that extend generally into the opening 251. These tabs 253 can be used to help retain and center the sample tube 106 during the insertion and removal of the extractor nozzle 130.

In the embodiment illustrated in FIG. 28, each sample rack 104 can be configured to releasably connect to an adjacent sample rack 104. As shown in FIG. 29, the body of the sample rack 104 can define a C-shape geometry. On the open end, there can be rounded tabs 239 that are axially aligned and protrude toward the inside of the C. The tabs 239 can include a tapered projection 241 on the leading edges to facilitate connecting adjacent sample racks 104. On the opposite end of the sample rack 104 there can be internal holes 243 that can be axially aligned. The tapered projection 239 can be cammed to engage with the respective holes 243. The C shape can allow the open end of the sample rack 104 to separate slightly when forced, and then return back to its original shape. To assemble a sample chain of sample racks 104, the open end of the sample rack 104 can be pressed into the opposite side of an adjacent sample rack 104 until the projections 241 of the tabs 239 on one sample rack 104 snap into the internal holes 243 in the adjacent sample rack 104. In other embodiments, other joints or connections are possible to relatively secure the plurality of sample racks 104.

Figure 31:
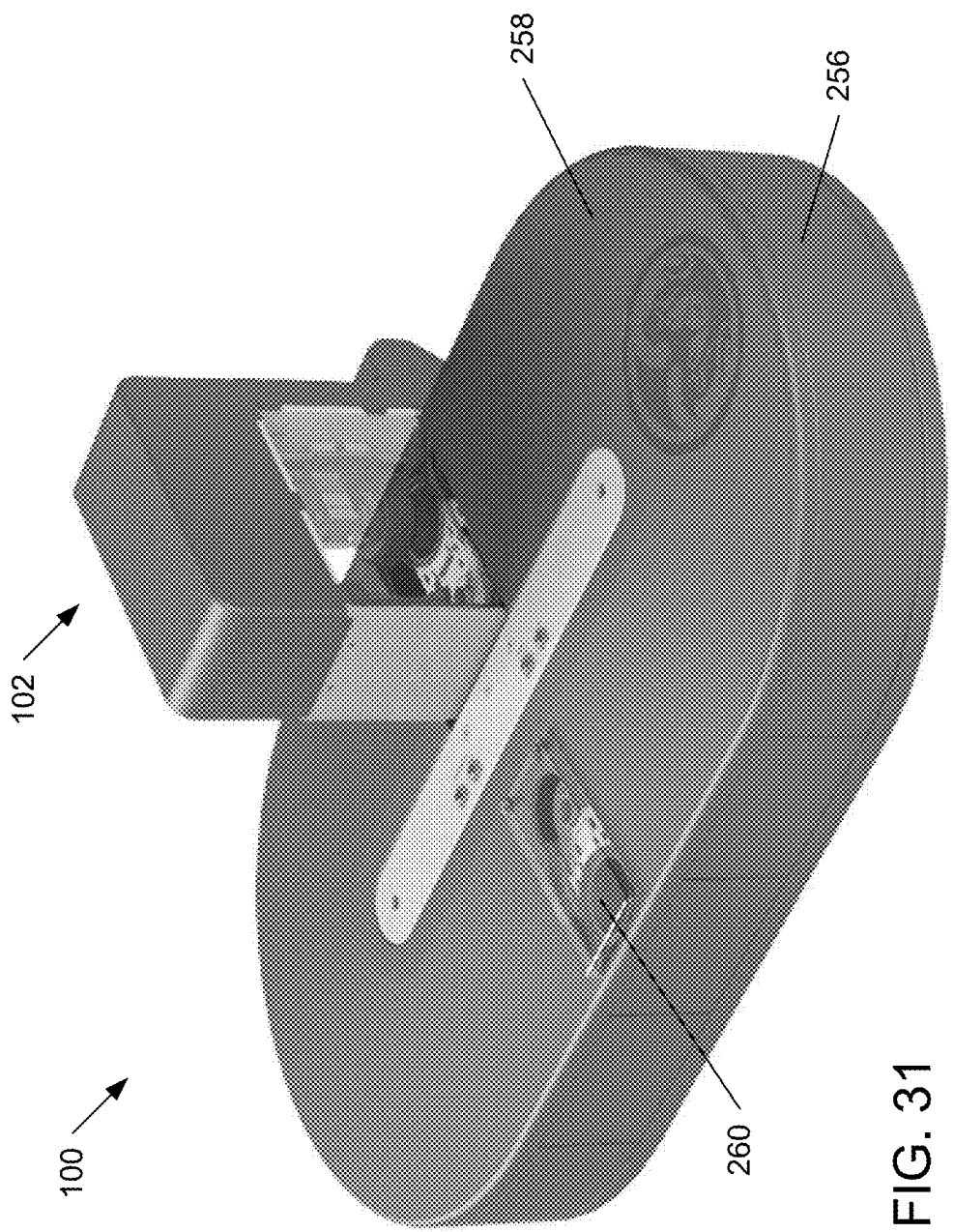
FIG. 31 is an isometric view of the fractionation system of FIG. 30 with a cover.

FIGS. 30-32 illustrate another embodiment of the fractionation system 100. The fractionation system 100 can include a body 256 to house the sample racks 104, extractor module 102, and drive system 168. With reference to FIG. 31, in some embodiments the fractionation system 100 can be configured as an enclosed assembly. A cover 258 can be secured around an open perimeter of the body 256 of the fractionation system 100 to cover the samples from outside contamination and debris. Removing the cover 258 can provide a user access to the entire drive system 168 as well as the drive motor for maintenance. In some embodiments, the cover 258 can include an access door 260. The access door 260 can be opened to access one or more sample racks 104, including a sample tube 106 and a filter cup 110.

As shown in FIG. 32, some embodiments of the extractor module 102 can include the filter assembly 108 positioned across from the extractor assembly 118. The filter assembly 108 can be secured to a linear actuator 140 to move the filter assembly 108 in the vertical direction and the extractor assembly 118 can be secured to the linear actuator 120 to move the extractor assembly 118 in the vertical direction. The linear actuator can move the movable carriage 122 of the extractor assembly 118. The movable carriage 122 can also include a sensor 124 that is stationary relative to the extractor nozzle 130. The sensor 124 can be calibrated to control movement of the linear actuator 120 so that the extractor nozzle does not extend beyond the light fraction material, or whatever depth or translucency of the sample tube 106 as set by an operator. As discussed throughout, given the benefit of this disclosure, one skilled in the art will appreciate that various types of sensors can be employed to achieve the desired extraction control.

As further shown in FIG. 32, embodiments of the fractionation system 100 can include a plurality of external connections 272. For example, the external connections 272 can include a deionized water supply and at least two vacuum connections. The at least two vacuum connections can be used to distinguish between recycled and wasted fluids. In use, the fractionation system 100 may require deionized water for tube rinsing and empty tube refill. Within the fractionation system 100, a water supply (e.g., the deionized water supply) can be split to two valves (e.g., solenoid valves). The example solenoid valves can control supply to the extractor nozzle 130 and the empty tube refill. In some embodiments, the vales may be normally closed and can be actuated (e.g., via controller signal) to supply either location.

In general, the fractionation system 100 according to any of the embodiments described herein can be configured to operate automatically (e.g., via software and algorithms executed by a controller). However, a user may interact with the fractionation system 100 to adjust settings and assist with loading and unloading samples. A user interface can include, for instance, a touch screen, a set of buttons, or other actuators mounted to or remotely linked to the fractionation system 100.

In some embodiments, an equipment user can have access to a single sample at a time via the access door 260 on the top cover 258. After a single sample is loaded/unloaded, the user can advance the chain one unit via a user interface. Applying an "Advance" command can progress the drive system 168 forward until the next sample rack 104 is aligned with the access door 260.

In some embodiments, the fractionation system 100 can be set up to run through a discrete number of sample racks 104 every cycle. There may be times, however, that the user would like to process a smaller discrete number of samples. This adjustment can be made via a user interface. The user can enter the number of samples, as well as the physical location of the first sample (indicated, for example, by an identifying character on the sample rack 104). This will signal to the controller which sample should be extracted first, and how many subsequent samples will follow. Alternatively, specific locations and a specific order can be programmed, in a manner that is not necessary serial along the chain of sample racks. In other embodiments, a user may select a continuous sample processing.

In general, depending on the makeup of the SOM in each sample, more or less rinse water may be needed to ensure the inner surface of the sample tube 106 is completely rinsed. This can be adjusted via a user interface by increasing or decreasing a rinse amount setting. In the same manner, the amount of water used to refill tubes after the SOM light fraction and residual fluid have been removed can be adjusted.

In certain implementations, a user may want to separate a known-density fluid from the rinse water used to clean the inner surface of the tube 106. Alternately, the user may want to combine these fluids into a single waste stream. This setting can also be adjusted within a user interface.

Figure 33:
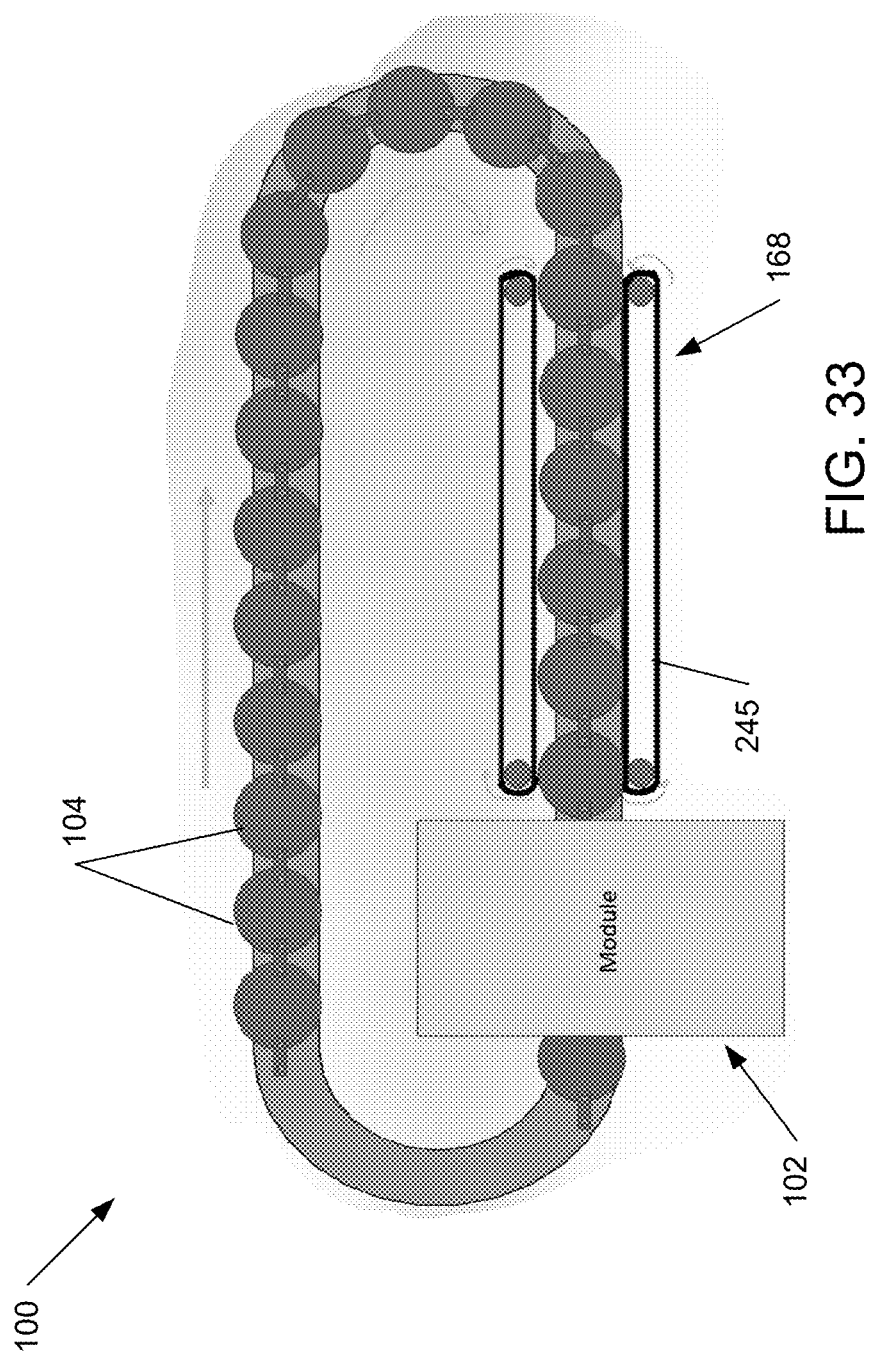
FIG. 33 is a top view of an exemplary drive system for a fractionation system according to an embodiment of the invention.
Figure 34:
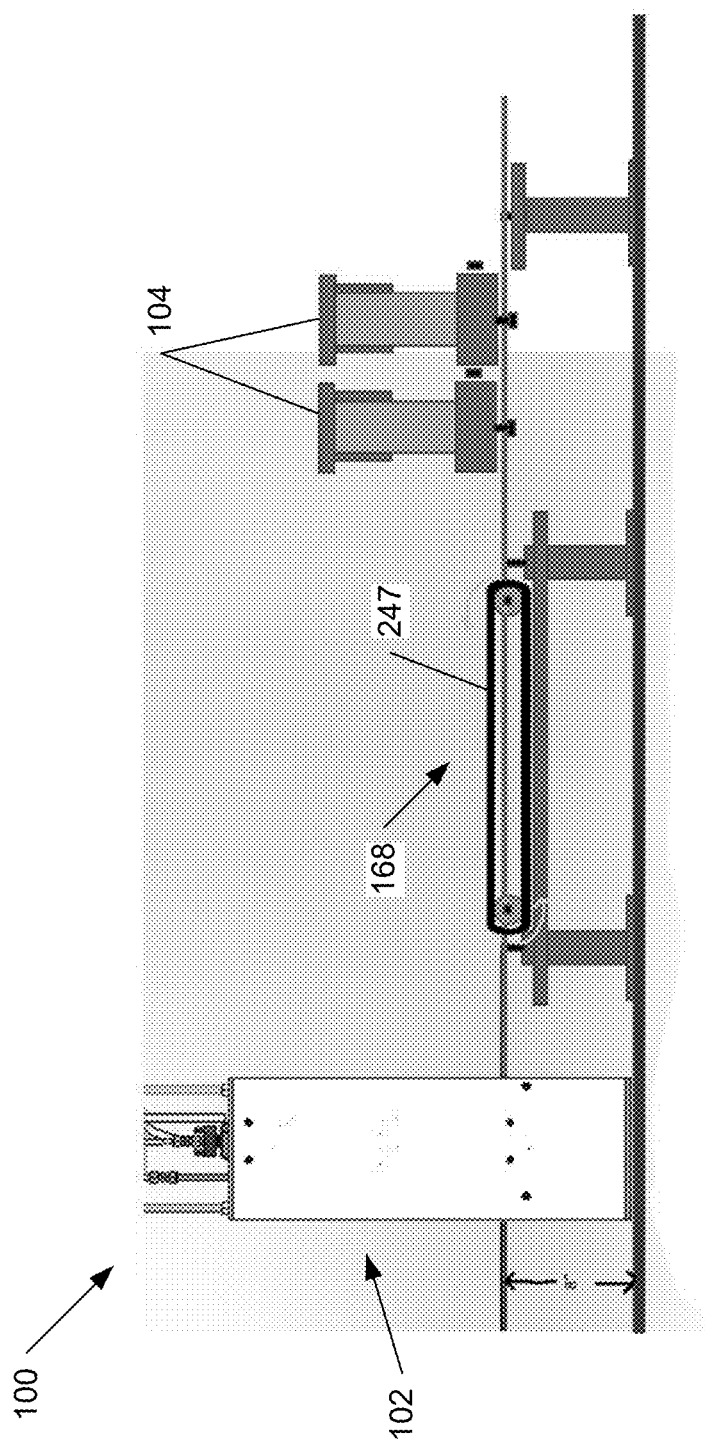
FIG. 34 is a side view of an exemplary drive system for a fractionation system according to another embodiment of the invention.

FIGS. 33 and 34 illustrate additional drive systems 168 and configurations according to other embodiments of the invention. It should be appreciated that the drive systems 168 illustrated in FIGS. 33 and 34 could be used in any of the fraction systems 100 described above. With reference to FIG. 33, the drive system 168 can include horizontal belts 245 (e.g., a pair of belts) that propel the sample racks 104 around the oval-shaped track 230. In this embodiment, the bottoms of the sample racks 104 may be suspended and not in contact with other components. FIG. 34 illustrates another embodiment of the drive system 168 including a single belt 247 that is configured to propel sample racks 104 around the track 230 and through the extractor module.

Various modifications and additions can be made to the exemplary embodiments discussed herein without departing from the scope of the disclosed subject matter. For example, while the embodiments described refer to particular features, the scope of this disclosure includes embodiments having different combinations of the features and embodiments that do not include all of the described features. Accordingly, the scope of the disclosed subject matter is intended to embrace all such alternatives, modifications, and variations, together with all equivalents thereof. Any of the embodiments or components thereof described herein may be modified to include any of the structures or methodologies disclosed in connection with different embodiments. Further, the present disclosure is not limited to a fractionation device type specifically shown. As noted previously, it will be appreciated by those skilled in the art that while the disclosure has been described above in connection with particular embodiments and examples, the disclosure is not necessarily so limited, and that numerous other embodiments, examples, uses, modifications and departures from the embodiments, examples and uses are intended to be encompassed by the claims attached hereto. Various features and advantages of the invention are set forth in the following claims.

The invention claimed is:

1. A soil fractionation system for separating fractions of soil, the soil fractionation system comprising:
a plurality of sample racks propelled by a drive system, each sample rack including:
a sample tube for holding a soil sample, the sample tube defining a sample tube opening; and
a filter cup for receiving an extracted fraction of the soil sample, the filter cup defining a filter cup opening at a top of the filter cup and having a filter disposed at a bottom of the filter cup,
an extractor module including:
an extractor assembly having an extractor nozzle dimensioned to be inserted into the sample tube; and
a filter assembly having a first filter sealing member dimensioned to sealingly engage the filter cup opening at the top of the filter cup and a second filter sealing member dimensioned to sealingly engage the filter cup at the bottom of the filter cup adjacent to the filter, and
a control system that controls:
relative positioning of the plurality of sample racks via the drive system;
relative movement between the extractor assembly and the sample tube; and
relative movement between the filter assembly and the filter cup.

2. The soil fractionation system of claim 1, wherein the extractor assembly is fluidly coupled to the filter assembly, and
wherein when the extractor assembly is inserted into the sample tube and the filter assembly is sealingly engaged with the filter cup, the sample tube and the filter cup are fluidly coupled.

3. The soil fractionation system of claim 1, wherein the extractor nozzle is disposed at a distal end of a conduit, and
wherein the extractor assembly includes a secondary cone, the extractor nozzle and the secondary cone forming an annular gap therebetween, the annular gap in fluid communication with the conduit.

4. The soil fractionation system of claim 3, wherein the extractor assembly includes a wiper that at least partially surrounds the extractor nozzle, the wiper having a leading edge configured to engage an interior surface of the sample tube.

5. The soil fractionation system of claim 3, wherein the extractor assembly includes a rinse system having an array of openings, the array of openings dimensioned to direct fluid toward the distal end of the conduit so that a rinsing fluid flows along an interior surface of the sample tube above the extractor nozzle.

6. The soil fractionation system of claim 1, wherein the extractor module includes at least one linear actuator, the at least one linear actuator configured to vertically displace one or more of the extractor assembly or the filter assembly toward one of the plurality of sample racks when the one of the plurality of sample racks is positioned within the extractor module.

7. The soil fractionation system of claim 1, further comprising:
a vacuum module adjacent to the second filter sealing member, the vacuum module configured to create a vacuum within the filter cup when the first filter sealing member is engaged with the filter cup opening at the top of the filter cup and the second filter sealing member is engaged with the filter cup at the bottom of the filter cup adjacent to the filter.

8. The soil fractionation system of claim 1, further comprising:
an indexing system having a first indexing member that is stationary relative to the extractor module and complementary indexing members disposed on the plurality of sample racks, the complementary indexing members movable relative to the extractor module via movement of the sample racks.

9. The soil fractionation system of claim 1, wherein the filter cup includes a floating flange, the floating flange movable in an axial and radial direction relative to the sample rack.

10. The soil fractionation system of claim 1, wherein the sample racks are movable about a continuous track.

11. An extractor module for a fractionation system, the extractor module comprising:
an extractor assembly having an extractor nozzle disposed at a distal end of a conduit, the extractor nozzle configured to be inserted into a soil sample having a light soil fraction suspended above a heavy soil fraction;
a filter assembly having first and second sealing members, the first sealing member fluidly coupled to a first tube and the second sealing member fluidly coupled to a vacuum chamber;
a first linear actuator configured for relative movement of the extractor assembly; and
and a second linear actuator configured for relative movement of the filter assembly.

12. The extractor module of claim 11, wherein the extractor assembly includes a wiper that at least partially surrounds the extractor nozzle and is formed from a flexible material.

13. The extractor module of claim 12, wherein the extractor assembly includes a sensor secured relative to the extractor nozzle, the sensor configured to sense soil density and signal to a controller to stop movement of the first linear actuator before the extractor nozzle reaches the heavy soil fraction.

14. The extractor module of claim 12, wherein the extractor assembly includes a rinse system spaced apart from the extractor nozzle and having an array of openings, the array of openings configured to direct fluid toward the distal end of the conduit.

15. The extractor module of claim 12, wherein the first sealing member includes a tapered end dimensioned to create a seal with a top of a filter cup.

16. The extractor module of claim 15, wherein the second sealing member is configured to create a seal with a bottom of the filter cup.

17. The extractor module of claim 12, wherein the filter assembly includes a biasing member adjacent to the first sealing member.

18. The extractor module of claim 12, wherein the filter assembly is configured to form a vacuum within a filter cup when the filter cup is engaged with the first and second sealing members.

19. A method of separating soil fractions, the method comprising:
moving a first sample rack having a sample tube and a filter cup into an extractor module;
inserting an extractor nozzle into the sample tube, the sample tube having a first soil fraction suspended above a second soil fraction;
moving a first sealing member into engagement with a top of a filter cup and moving a second sealing member into engagement with a bottom of the filter cup;
forming a vacuum within the filter cup;
transferring via the vacuum the first soil fraction from the sample tube to the filter cup through a conduit that fluidly couples the extractor nozzle to the first sealing member;
removing the extractor nozzle from the sample tube and disengaging the first and second sealing members from the filter cup; and
moving a second sample rack into the extractor module.

20. The method of claim 19, wherein before removing the extractor nozzle from the sample tube, a rinse system provides fluid into the sample tube above the extractor nozzle and the fluid flows into sidewall channels of the extractor nozzle and is transferred to the filter cup through the conduit.

* * * * *

UNITED STATES PATENT AND TRADEMARK OFFICE
CERTIFICATE OF CORRECTION

PATENT NO. : 12,326,460 B2
APPLICATION NO. : 18/094254
DATED : June 10, 2025
INVENTOR(S) : Maria Francesca Cotrufo et al.

Page 1 of 1

It is certified that error appears in the above-identified patent and that said Letters Patent is hereby corrected as shown below:

In the Claims

Claim 11, Line 6-7, Column 20, "movement of the extractor assembly; and and a second linear" should be –movement of the extractor assembly; and a second linear–.

Claim 13, Line 13, Column 20, "The extractor module of claim 12," should be –The extractor module of claim 11,–.

Claim 14, Line 18, Column 20, "The extractor module of claim 12," should be –The extractor module of claim 11,–.

Claim 15, Line 23, Column 20, "The extractor module of claim 12," should be –The extractor module of claim 11,–.

Claim 17, Line 29, Column 20, "The extractor module of claim 12," should be –The extractor module of claim 11,–.

Claim 18, Line 32, Column 20, "The extractor module of claim 12," should be –The extractor module of claim 11,–.

Signed and Sealed this
Fifth Day of August, 2025

Coke Morgan Stewart
*Acting Director of the United States Patent and Trademark Office*